(12) United States Patent
Hartwig et al.

(10) Patent No.: US 9,701,635 B2
(45) Date of Patent: Jul. 11, 2017

(54) C-H FLUORINATION OF HETEROCYCLES WITH SILVER (II) FLUORIDE

(71) Applicant: THE REGENTS OF THE UNIVERSITY OF CALIFORNIA, Oakland, CA (US)

(72) Inventors: John Hartwig, Berkeley, CA (US); Patrick Fier, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 82 days.

(21) Appl. No.: 14/907,694

(22) PCT Filed: Jul. 28, 2014

(86) PCT No.: PCT/US2014/048472
§ 371 (c)(1),
(2) Date: Jan. 26, 2016

(87) PCT Pub. No.: WO2015/013715
PCT Pub. Date: Jan. 29, 2015

(65) Prior Publication Data
US 2016/0185723 A1    Jun. 30, 2016

Related U.S. Application Data

(60) Provisional application No. 61/859,116, filed on Jul. 26, 2013.

(51) Int. Cl.
| | | |
|---|---|---|
| C07D 493/00 | (2006.01) |
| C07D 213/61 | (2006.01) |
| C07D 401/04 | (2006.01) |
| C07D 239/46 | (2006.01) |
| C07D 213/63 | (2006.01) |
| C07D 213/65 | (2006.01) |
| C07D 213/75 | (2006.01) |
| C07D 213/79 | (2006.01) |
| C07D 213/80 | (2006.01) |
| C07D 213/803 | (2006.01) |
| C07D 213/81 | (2006.01) |
| C07D 213/82 | (2006.01) |
| C07D 215/18 | (2006.01) |
| C07D 239/42 | (2006.01) |
| C07D 405/04 | (2006.01) |

(52) U.S. Cl.
CPC ......... *C07D 213/61* (2013.01); *C07D 213/63* (2013.01); *C07D 213/65* (2013.01); *C07D 213/75* (2013.01); *C07D 213/79* (2013.01); *C07D 213/80* (2013.01); *C07D 213/803* (2013.01); *C07D 213/81* (2013.01); *C07D 213/82* (2013.01); *C07D 215/18* (2013.01); *C07D 239/42* (2013.01); *C07D 239/46* (2013.01); *C07D 401/04* (2013.01); *C07D 405/04* (2013.01)

(58) Field of Classification Search
None
See application file for complete search history.

(56) References Cited

U.S. PATENT DOCUMENTS

| | | | |
|---|---|---|---|
| 4,567,273 A * | 1/1986 | Fung .................... | C07D 213/61 546/345 |
| 7,202,388 B2 * | 4/2007 | Grushin ................. | C07B 39/00 570/147 |

FOREIGN PATENT DOCUMENTS

WO    WO 2015/013715    1/2015

OTHER PUBLICATIONS

Akita, H. et al., *Tetrahedron-Asymmetry* 2006, 17, 1705.
Bell, T. W.; et al., *J. Org. Chem.* 1987, 52, 3847.
Bobbio, C.; Schlosser, M. *J. Org. Chem.* 2005, 70, 3039.
Bonnet, V. et al., *Tetrahedron* 2002, 58, 4429.
Bradlow, H. I.; Vanderwerf, C. A. *J. Org. Chem.* 1949, 14, 509.
Chambers, R. D. et al., J. S. *J Chem Soc Perk T 1* 1999, 803.
Cherng, Y. H. *Tetrahedron* 2002, 58, 4931.
Coffen, D. L. et al., *J. Org. Chem.* 1984, 49, 5109.
Dolci, L. et al., *J Labelled Compd Rad* 1999, 42, 975.
Dolle, F. et al., *J Labelled Compd Rad* 1998, 41, 451.
Erian, A. W., *J Heterocyclic Chem*, 2001, 38, 793.
Estel, L. et al., *J. Org. Chem.* 1988, 53, 2740.
Gungor, T. et al., *J. Organomet. Chem.* 1981, 215, 139.
Hartwig, J. F. *Acc. Chem. Res.* 2012, 45, 864.
Honda, T. et al., *Heterocycles* 2003, 59, 169.
Inkster, J. et al., *J Labelled Compd Rad* 2008, 51, 444.
Kauffmann, T. et al., *Chem Ber-Recl* 1983, 116, 992.(Abstract).
Karramkam, M. et al., *J Labelled Compd Rad* 2003, 46, 979.
Klapars, A.; et al., *J. Org. Chem.* 2005, 70, 10186.
Kling, A. et al. *Bioorg. Med. Chem.* 2003, 11, 1319.
Li, X. et al., *Org Biomol Chem* 2003, 1, 4392.
Loupy, A. et al., *Heterocycles* 1991, 32, 1947.
Ohta, S. et al., *Synthesis-Stuttgart* 1982, 833.

(Continued)

*Primary Examiner* — Heidi Reese
(74) *Attorney, Agent, or Firm* — Morgan, Lewis & Bockius LLP; Jeffry S. Mann

(57) ABSTRACT

The present invention provides compositions and methods for the selective C—H fluorination of nitrogen-containing heteroarenes with $AgF_2$, which has previously been considered too reactive for practical, selective C—H fluorination. Fluorinated heteroarenes are prevalent in numerous pharmaceuticals, agrochemicals and materials. However, the reactions used to introduce fluorine into these molecules require pre-functionalized substrates or the use of $F_2$ gas. The present invention provides a mild and general method for the C—H fluorination of nitrogen-containing heteroarene compounds to 2-fluoro-heteroarenes with commercially available $AgF_2$. In various embodiments, these reactions occur at ambient temperature within one hour and occur with exclusive selectivity for fluorination at the 2-position. Exemplary reaction conditions are effective for fluorinating diazine heteroarenes to form a single fluorinated isomer.

19 Claims, No Drawings

(56) References Cited

OTHER PUBLICATIONS

Schmid, G. H.; Wolkoff, A. W., Can. *J. Chem.* 1972, 50, 1181.
Schlosser, M.; Rausis, T. *Helvetica Chimica Acta* 2005, 88, 1240.
Seki, K. et al., *Heterocycles* 1994, 37, 993.
Thomas, S. et al., *Org. Lett.* 2003, 5, 3867.
Vanderpuy, M. *Tetrahedron Lett* 1987, 28, 255.
Weitgenant, J. et al., *P. Org. Lett.* 2005, 7, 3609.
Wittman, M. et al., *J. Med. Chem.* 2009, 52, 7360.
Zweig, A. et al., *J. Org. Chem.* 1980, 45, 3597.

* cited by examiner

C-H FLUORINATION OF HETEROCYCLES WITH SILVER (II) FLUORIDE

CROSS-REFERENCE TO RELATED APPLICATIONS

This application claims under 35 USC 119(e) the benefit of U.S. Provisional Application No. 61/859,116, filed Jul. 26, 2013, which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under Grant No. GM-55382 awarded by the National Institutes of Health. The Government has certain rights in the invention.

BACKGROUND OF THE INVENTION

Fluorinated heterocycles are an important class of compounds found in biologically active molecules and materials (a. Erian, A. W., *J Heterocyclic Chem*, 2001, 38, 793; b. Kirsch, P., *Modern fluoroorganic chemistry: synthesis, reactivity, applications*; Wiley-VCH; Weinheim; Great Britain, 2004; c. Bégué, J.-P.; Bonnet-Delpon, D., *Bioorganic and Medicinal Chemistry of Fluorine*; John Wiley & Sons: Hoboken, N.J., 2008). The selective introduction of fluorine into small molecules can lead to subtle or profound effects on the conformation, solubility and stability of a molecule compared to the non-fluorinated counterpart. The introduction of fluorine into a basic heterocycle can modulate the basicity and binding properties with only a small change in the steric environment. These effects are especially prevalent in 2-fluoropyridines because of the close proximity of fluorine and nitrogen. One example of the influence of fluorine in the 2-position of a pyridine is seen in the improved potency, cell activity, and selectivity of the 2-fluoropyridyl containing anti-cancer compound BMS-754807 compared to the non-fluorinated analogue (Wittman, M. D.; Carboni, J. M.; Yang, Z.; Lee, F. Y.; Antman, M.; Attar, R.; Balimane, P.; Chang, C. Y.; Chen, C.; Discenza, L.; Frennesson, D.; Gottardis, M. M.; Greer, A.; Hurlburt, W.; Johnson, W.; Langley, D. R.; Li, A. X.; Li, J. Q.; Liu, P. Y.; Mastalerz, H.; Mathur, A.; Menard, K.; Patel, K.; Sack, J.; Sang, X. P.; Saulnier, M.; Smith, D.; Stefanski, K.; Trainor, G.; Velaparthi, U.; Zhang, G. F.; Zimmermann, K.; Vyas, D. M., *J. Med. Chem.* 2009, 52, 7360). 2-Fluoropyridines enriched in $^{18}$F are valuable as radiotracers in PET imaging (a. Dolle, F.; Valette, H.; Bottlaender, M.; Hinnen, F.; Vaufrey, F.; Guenther, I.; Crouzel, C., *J Labelled Compd Rad* 1998, 41, 451; b. Dolci, L.; Dolle, F.; Jubeau, S.; Vaufrey, F.; Crouzel, C., *J Labelled Compd Rad* 1999, 42, 975; c. Karramkam, M.; Hinnen, F.; Vaufrey, F.; Dolle, F., *J Labelled Compd Rad* 2003, 46, 979; d. Inkster, J. A. H.; Guerin, B.; Ruth, T. J.; Adam, M. J., *J Labelled Compd Rad* 2008, 51, 444).

Moreover, 2-fluoropyridines exhibit unique reactivity as synthetic intermediates compared to other halogenated pyridines. Thus, a convenient route to 2-fluoroazines allows the preparation of 2-amino, alkoxy, and alkyl azines, as well as pyridines containing halogens and additional functionality at the other positions of the ring for further manipulations.

The conditions typically used to form heteroaryl-fluorine bonds are harsh; thus the fluorine is usually introduced into the heteroarene ring at the beginning of a synthesis or as part of a building block. Improved methods for late-stage heteroaromatic fluorination would be important for diversification in medicinal chemistry. Moreover, methods for heteroaromatic fluorination with simple fluoride sources would be valuable for the preparation of $^{18}$F labeled compounds used in PET imaging. Yet, no general method has been reported for the fluorination of aryl halides.

Although 2-fluoroazines have favorable physical properties and are valuable synthetic intermediates, they are difficult to prepare when the azine contains other functional groups. The most practiced laboratory methods for the synthesis of 2-fluoropyridines are the Balz-Schiemann reaction of 2-aminopyridines and nucleophilic aromatic substitution of electron-deficient 2-chloro or 2-nitropryidines with an anhydrous fluoride source (Scheme 1). While these methods are useful for the synthesis of simple 2-fluoropyridines, the strongly acidic or basic reaction conditions and the need for pre-functionalized substrates limit their synthetic utility. The direct fluorination of pyridines and diazines with $F_2$ is also known. However, the use of $F_2$ gas is not practical in a typically laboratory setting because of the hazards associated with this gas, and the reactions with $F_2$ occur in low yield, often give a mixture of products, and have only been demonstrated with very simple substrates.

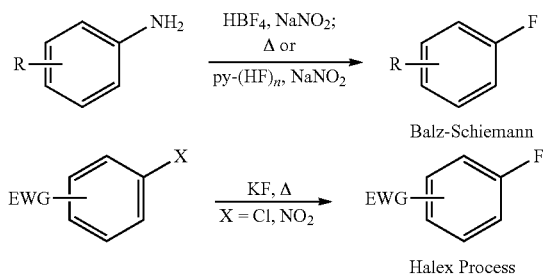

Scheme 1. Conventional Routes to Fluoroarenes

Accordingly, a reaction that directly fluorinates a nitrogen-containing heteroarene precursor to form the corresponding fluorinated heteroarene at low to modest temperatures (e.g., <100° C.) would represent a significant advance in the art of heterorene fluorination and the provision of nitrogen-containing fluoroheteroarenes. Further, a reaction that leads to the mono-fluorination of a nitrogen-containing heteroarene precursor at a positions α- to the nitrogen would be of considerable utility, due to the strong influence of the introduced fluorine on the electronic properties of the nitrogen and the ability to replace this fluorine with common nucleophiles Moreover, such a reaction that did not degrade or react appreciably with substituents on the heteroarene nucleus would also be of great value. Surprisingly, the present invention provides such a reaction, compositions of use in carrying out this reaction and fluorinated nitrogen-containing heteroarene compounds prepared by the reaction.

SUMMARY OF THE INVENTION

The present invention provides compositions and methods for fluorinating functionally diverse heteroarenes (e.g., nitrogen atom-containing heteroarenes). An exemplary heteroarene is a six-membered aromatic compound containing a nitrogen atom. In various embodiments, the invention provides a method for fluorination of a heteroarene precursor compound with $AgF_2$ in an organic solvent under ambient or slightly elevated temperature. The invention provides a mild and practical method for the selective C—H fluorination of a variety of nitrogen-containing heteroarenes, e.g., pyridine, di- and tri-azines with a single, commercially available reagent. In exemplary embodiments, these reactions occur within about one hour at approximately room temperature, are trivial to perform, and produce easily separable products. In various embodiments, the reaction occurs in the presence of a readily available organic solvent. In an exemplary embodiment, the solvent does not itself include a fluorine atom. In various embodiments, the fluorination occurs at a carbon atom adjacent the nitrogen atom (i.e., α to the nitrogen atom).

In an exemplary embodiment, the nitrogen-containing heteroarene precursor compound has the formula:

wherein A is selected from N and $CR^4$; D is selected from N and $CR^5$; E is selected from N and $CR^6$; G is selected from N and $CR^7$; and J is selected from N and $CR^8$. $R^4$, $R^5$, $R^6$, $R^7$ and $R^8$ are independently selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$, $NR^9C(O)NR^{10}R^{11}$, $C(NR^9)R^{10}$, and $-NO_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

In various embodiments, $R^9$, $R^{10}$, and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^9$, $R^{10}$, and $R^{11}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

In an exemplary embodiment, this invention allows for the direct synthesis of nitrogen-containing 2-fluoroheteroaryl compounds from a broad range of nitrogenous heterocycles through C—H fluorination of the heteroaryl moiety with $AgF_2$. As discussed above, nitrogen-containing heteroaryl fluorides are ubiquitous in chemistry, yet methods for the synthesis of 2-heteroaryl fluorides are limited to fluoro-dediazotization (Balz-Schiemann reaction) and nucleophilic aromatic substitution reactions of 2-heteroaryl halides. Thus, the present invention represents a significant advance in this important field of chemistry.

In an exemplary embodiment, the invention provides compositions for conducting reactions, and reactions themselves, utilizing $AgF_2$ as a fluorination reagent. Exemplary reactions occur rapidly near room temperature, without any additional reagents, and/or occur with exclusive selectivity to form a single isomeric product. These reactions offer advantages over other methods for forming nitrogen-containing 2-fluoroheteroarenes because of the mild reaction conditions and the lack of prefunctionalization of the substrates. In various embodiments, the invention provides fluorinated nitrogen-containing heteroarenes that are structurally novel.

In an exemplary embodiment, the fluorinated compound (e.g., produced by a method of the invention) is used as a precursor in one or more $S_NAr$ reactions in which the fluorine atom is replaced by a nucleophilic reactant. Exemplary nucleophiles are carbon, oxygen, nitrogen and sulfur nucleophiles. The only limitation on the nucleophiles of use in this embodiment is that they be sufficiently strong electron donors to displace the fluorine from the C—F bond. Those of skill in the art, with a fluorinated analogue in hand can readily determine whether a nucleophile effectively displaces the fluorine from the C—F bond using methods recognized in the art and without recourse to undue experimentation.

Additional objects, embodiments and advantages of the present invention are set forth in the detailed description that follows.

DETAILED DESCRIPTION OF THE INVENTION

I. Introduction

The ability to selectively fluorinate a heteroarene substrate has broad application, especially in the agricultural, pharmaceutical, and polymer industries. As described herein, the present invention relates to compositions and methods for transforming a heteroarene precursor compound to the corresponding fluoro analogue. The compositions and methods of the invention utilize simple, readily available substrates and reaction mixtures and, thus, have wide applicability.

In various embodiments, the present invention provides a reaction mixture of use in a one-step procedure for the fluorination of a nitrogen-containing heteroarene precursor compound. The reaction occurs with readily available and non-hazardous reagents. This reaction tolerates a wide range of substituents on the core, e.g., amine, ether, amide, ester, aromatic bromide and protected alcohol functionalities, and occurs in high yield even with sterically hindered substrates. The simplicity and generality of this method makes it attractive for the introduction of fluoride into functionally diverse heteroarene compounds.

In addition to the reaction mixtures, there is provided a method of utilizing such a reaction mixture to prepare a heteroaryl fluoride compound. In general terms, the method includes incubating the reaction mixture under conditions sufficient to form the heteroaryl fluoride.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

Where substituent groups are specified by their conventional chemical formulae, written from left to right, the structures optionally also encompass the chemically identical substituents, which would result from writing the structure from right to left, e.g., —CH$_2$O— is intended to also optionally recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated C$_{9-10}$, oleoyl chain or the diunsaturated C$_{9-10, 12-13}$ linoeyl chain.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

As used herein, "heteroarene" refers to a molecule having a reactive heteroaromatic core including one or more intra-annular nitrogen atoms. Exemplary heteroarenes are six-membered rings. This term encompasses diverse compounds, for example, substituted or unsubstituted pyridine, substituted or unsubstituted diazines (i.e., including two intra-annular nitrogen atoms), and substituted or unsubstituted triazines (i.e., including three intra-annular nitrogen atoms). Because heteroarene and heteroaryl describe, respectively, a parent molecule and a substituent formed from the parent molecule, these terms are not mutually exclusive terms and the structures of their reactive aromatic cores are co-extensive. Thus, the discussion regarding "heteroaryl" immediately above is germane to the definition of "heteroarene".

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl, "heteroaryl", and "heteroarene") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. Each of the above-named groups is attached to the heteroarene or heteroaryl nucleus directly or through a or a heteroatom (e.g., P, N, O, S, Si, or B); and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

Two of the substituents on adjacent atoms of the aryl, heteroarene or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl, heteroarene or heteroaryl ring may optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted (C$_1$-C$_6$)alkyl. These terms encompass groups considered exemplary "aryl group substituents", which are components of exemplary "substituted aryl" "substituted heteroarene" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The terms "substrate" and "precursor" are used interchangeably and refer to a nitrogen-containing heteroarene precursor substitutable by a fluorine synthon in a method and composition of the invention. An exemplary substrate or precursor is a six-membered nitrogen-containing heteroarene compound such as pyridine, a diazine or a triazine, which can react under the conditions of the invention, to yield at least one product having a fluoro moiety. Exemplary diazines are substituted or unsubstituted 1,4-, 1,3- and 1,2-diazine. An exemplary triazine is a substituted or unsubstituted 1,2,3-, 1,2,4- and 1,3,5-triazine. An exemplary triazine is a substituted triazine.

As used herein, "nitrogen-containing heteroarene precursor" refers to a molecule having a reactive core heteroarene system with at least one nitrogen within the ring of the heteroarene system. This definition further includes diazines and triazines.

The term "2-fluoro analogue" refers to a heteroarene compound including a six-membered nitrogen-containing ring system in which a fluoro atom is bound to a carbon atom immediately adjacent to an intraannular nitrogen atom of the ring system. For purposes of clarity, "2-fluoro analogue" does not include polyfluorinated analogues of the nitrogen-containing heteroarene.

The term "organic solvent" refers to solvents that do not include a fluoro moiety within their molecular structure. For purposes of clarity, "organic solvent" does not include perfluorinated amines or perfluorinated cyclic ethers.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

Below are examples of specific embodiments for carrying out the present invention. The examples are offered for illustrative purposes only, and are not intended to limit the scope of the present invention in any way.

III. The Compositions

In an exemplary embodiment, the invention provides a reaction mixture that includes a nitrogen-containing heteroarene precursor, AgF$_2$ and an organic solvent. In an exemplary embodiment, the solvent is CH$_3$CN. In various embodiments, the heteroarene is substituted or unsubstituted pyridine, a substituted or unsubstituted diazine or a substituted or unsubstituted triazine. In various embodiments, the nitrogen-containing heteroarene precursor is mono-chlorinated at the position a to a nitrogen atom of the precursor.

The reaction mixture functions to transform nitrogen-containing heteroarene substrates of a broad range of structures to the corresponding mono-fluorinated analogue. The precursor is optionally substituted, for example, with an amine, ether, amide, carboxylic acid, ester, halide, protected alcohol or a combination thereof. In an exemplary embodiment, the reaction mixture transforms the precursor into a 2-fluoro analogue of the precursor.

In an exemplary embodiment, the nitrogen-containing heteroarene precursor compound has the formula:

wherein A is selected from N and $CR^4$; D is selected from N and $CR^5$; E is selected from N and $CR^6$; G is selected from N and $CR^7$; and J is selected from N and $CR^8$. $R^4$, $R^5$, $R^6$, $R^7$ and $R^8$ are independently selected from H, and an aryl group substituent as that term is defined herein. Exemplary aryl group substituents include substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$, $NR^9C(O)NR^{10}R^{11}$, $C(NR^9)R^{10}$, and $-NO_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

In various embodiments, $R^9$, $R^{10}$, and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^9$, $R^{10}$, and $R^{11}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

In an exemplary embodiment, two, three, four or five of $R^4$, $R^5$, $R^6$, $R^7$, and $R^8$ are CH.

In various embodiments, the precursor has the formula:

in which the moieties D, E, G and J are as set forth above.

In exemplary embodiments, the precursor compound has a formula selected from:

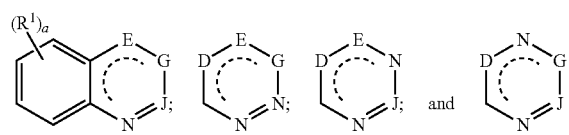

in which the moieties D, E, G and J are as set forth above. Each $R^1$ is independently selected from aryl group substituents as that term is defined herein, e.g., substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^2R^3$, $-NR^2R^3$, $-OR^2$, $-S(O)_2R^2$, $-C(O)R^2$, $-COOR^2$, $-CONR^2R^3$, $-S(O)_2OR^2$, $-OC(O)R^2$, $-C(O)NR^2R^3$, $-NR^2C(O)R^3$, $-NR^2SO_2R^3$, $NR^2C(O)NR^3R^{12}$, $C(NR^2)R^3$, and $-NO_2$, wherein two or more $R^1$ moieties together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. The index a is an integer from 0 to 4.

In various embodiments, $R^2$, $R^3$ and $R^{12}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^2$, $R^3$ and $R^{12}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

In an exemplary embodiment, the reaction mixture further includes fluorinated product derived from the precursor through the method of the invention (e.g., the 2-fluoro analogue of the precursor). Exemplary products are of the formula:

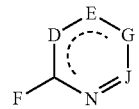

in which the moieties D, E, G and J are as described herein.

In various embodiments, there is provided a fluorinated compound according to the formula above, which is produced by a method of the invention, using a reaction mixture according to the invention. In an exemplary embodiment, this compound is a novel compound. Exemplary compounds produced by a method of the invention are essentially pure. In various embodiments, the compound is in a purer state than that known in the art for such compound produced by methods other than the method of the invention. In various embodiments, the novel compound, the fluorinated compounds which are essentially pure or are purer than art-recognized compounds are produced by a method according to the invention.

In an exemplary embodiment, the precursor includes a carboxylic acid substituent, which is converted in the product to an acyl fluoride.

In various embodiments, the invention provides a reaction mixture in which the heteroarene precursor, and $AgF_2$ are present in the reaction mixture in a ratio which is from about 1:1 to about 1:5, e.g., 1:4, 1:3, or 1:2. In an exemplary embodiment, the ratio is about 1 to about 3.

In an exemplary embodiment, the invention provides a fluorinated compound prepared by a method of the invention. In various embodiments, the compound is a compound according to Table 2.

IV. The Methods

In various embodiments, the present invention provides methods for converting a nitrogen-containing heteroarene precursor compound to a fluoro-substituted analogue. In an exemplary embodiment, the analogue is the 2-fluoro analogue of the nitrogen-containing precursor compound. In an exemplary embodiment, the method includes: (a) forming a reaction mixture as set forth herein; and (b) incubating the reaction mixture under conditions appropriate to form the fluoro-substituted analogue of the nitrogen-containing heteroarene precursor compound.

According to the method of the invention, appropriate methods include any useful temperature or range of temperatures that can be used to convert the precursor to the desired product. In various embodiments, the temperature is from about 0° C. to about 100° C. or from about 10° C. to about 50° C. In an exemplary embodiment, the reaction is performed at ambient temperature, i.e., about 25° C.

According to the method of the invention, the reaction mixture can be incubated for any useful length of time. In various embodiments, the invention is incubated at a desired temperature for about 1 hour to about 36 hours, e.g., for about 6 hours to about 24 hours. In various embodiments, incubation for about one hour is sufficient to produce significant conversion of the precursor to the corresponding fluorinated analogue.

In various embodiments, the reaction proceeds in the absence of added base. This does not preclude the substrate including one or more basic moiety. For purposes of clarity an arene precursor substituent the includes a basic moiety is not to be considered an "added base".

The reaction mixture can be incubated in a vessel of any useful configuration. In an exemplary embodiment, the vessel and its contents are not protected from light during the reaction. In this embodiment, there is essentially no difference in the yield of the desired 2-fluoro analogue between reaction conditions in which the reaction mixture is protected from light and reaction conditions in which the reaction mixture is not protected from light.

In addition to the value of 2-fluoro-heteroarenes (e.g., 2-fluoropyridines) as a final product, these compounds are valuable synthetic intermediates (Scheme 4). A fluorine atom in the 2-position of a heteroarene (e.g., pyridines and di- and tri-azines) allows several transformations to be conducted that cannot be conducted on the parent heteroarene or other derivatives. For example, 2-fluoropyridines undergo selective lithiation in the 3-position of the ring with LDA, and the resulting 3-pyridyl anion can be quenched with a variety of electrophiles (a. Gungor, T.; Marsais, F.; Queguiner, G. *J. Organomet. Chem.* 1981, 215, 139; b. Estel, L.; Marsais, F.; Queguiner, G. *J. Org. Chem.* 1988, 53, 2740; cBobbio, C.; Schlosser, M. *J. Org. Chem.* 2005, 70, 3039). 2-Fluoropyridines can also undergo acid catalyzed hydrolysis to 2-pyridones (Bradlow, H. I.; Vanderwerf, C. A. *J. Org. Chem.* 1949, 14, 509). Thus, the fluorination chemistry of pyridines described herein can be applied in two-step syntheses of diversely functionalized 3-substituted pyridines or 2-pyridones.

However, the most common reactions of 2-fluoropyridines are nucleophilic substitutions with a range of carbon and heteroatom nucleophiles (a. Cherng, Y. H. *Tetrahedron* 2002, 58, 4931; b. Kling, A.; Backfisch, G.; Delzer, J.; Geneste, H.; Graef, C.; Hornberger, W.; Lange, U. E. W.; Lauterbach, A.; Seitz, W.; Subkowski, T. *Bioorg. Med. Chem.* 2003, 11, 1319; c. Thomas, S.; Roberts, S.; Pasumansky, L.; Gamsey, S.; Singaram, B. *Org. Lett.* 2003, 5, 3867; d. Kauffmann, T.; Mitschker, A.; Woltermann, A. *Chem Ber-Recl* 1983, 116, 992; e. Loupy, A.; Philippon, N.; Pigeon, P.; Galons, H. *Heterocycles* 1991, 32, 1947). In contrast to the order of reactivity of alkyl halides, fluoroarenes are more reactive than the other haloarenes. With a method to prepare 2-fluoropyridines through C—H functionalization, substitution chemistry can now be conducted in the presence of other halogens or electrophilic functionality. The synthesis of the anti-diabetic drug Rosiglitazone is one pharmaceutical compound prepared from a 2-fluoropyridine (Li, X.; Abell, C.; Warrington, B. H.; Ladlow, M. *Org Biomol Chem* 2003, 1, 4392). In addition, 2-fluoropyridines have been used in the total synthesis of non-fluorinated compounds, including camptothecin. Thus, the 2-fluoroarenes, e.g., 2-fluoropyridines, formed by the present fluorination process can be converted to a variety of 2-functionalized heteroarenes, e.g., 2-functionalized pyridines (Scheme 4).

Thus, in an exemplary embodiment, the invention provides a method of preparing a compound using a nitrogen-containing fluoroheteroarene of the invention as an intermediate in the preparation. In various embodiments, the invention provides a compound prepared by reaction of a fluoro-heteroarene compound prepared by the method of the invention. In an exemplary embodiment, the fluoro-heteroarene compound is a 2-fluoro-heteroarene. In an exemplary embodiment, the method of the invention does not add fluorine in any appreciable amount to a position other than the 2-position adjacent a nitrogen atom in a nitrogen atom-containing heteroarene.

In an exemplary embodiment, the fluorinated compound (e.g., produced by a method of the invention) is used as a precursor in one or more $S_NAr$ reactions in which the fluorine atom is replaced by a nucleophilic reactant (see, e.g., Example 2). Exemplary nucleophiles are carbon, oxygen, nitrogen and sulfur nucleophiles. The only limitation on the structure of the nucleophiles of use in this embodiment is that the nucleophiles be sufficiently strong electron donors that they can displace the fluorine from the C—F bond. Those of skill in the art, with a fluorinated analogue in hand, can readily determine whether a nucleophile effectively displaces the fluorine from the C—F bond using methods recognized in the art and without recourse to undue experimentation.

The following examples illustrate embodiments of the invention and are not intended to limit the scope of the compositions of the invention or the methods in which they find use.

Examples

Example 1

I. Materials and Methods

All manipulations were conducted under an inert atmosphere with a nitrogen-filled glovebox unless otherwise noted. All reactions were conducted in oven-dried vials fitted with a Teflon-lined screw cap under an atmosphere of nitrogen unless otherwise noted.

Silver difluoride ($AgF_2$) was purchased from Alfa Aesar and used as received. Acetonitrile was distilled from $CaH_2$ and stored over molecular sieves. Unless otherwise noted, all other reagents were purchased from commercial suppliers and used as received. 2-tert-butylpyridine (Ic) (Bell, T. W.; Hu, L. Y.; Patel, S. V., J. Org. Chem. 1987, 52, 3847), 2-(2-methyl-1,3-dioxolan-2-yl)pyridine (1k) (Honda, T.; Namiki, H.; Kudoh, M.; Nagase, H.; Mizutani, H., Heterocycles 2003, 59, 169), 2-pyridylmethyl acetate (1l) (Weitgenant, J. A.; Mortison, J. D.; Helquist, P. Org. Lett. 2005, 7, 3609), 3-(2-methyl-1,3-dioxolan-2-yl)pyridine (1u) (Coffen, D. L.; Hengartner, U.; Katonak, D. A.; Mulligan, M. E.; Burdick, D. C.; Olson, G. L.; Todaro, L. J., J. Org. Chem. 1984, 49, 5109), tert-butyl nicotinate (1v) (Ohta, S.; Shimabayashi, A.; Aono, M.; Okamoto, M., Synthesis-Stuttgart 1982, 833), 4-chloropyridine (1y) (Schmid, G. H.; Wolkoff, A. W., Can. J. Chem. 1972, 50, 1181), toluene-4-sulfonic acid-2-(5-ethylpyridin-2-yl)-ethyl ester (1ai) (Chhangamal, C. V.; Rameshchan, P. R.; Budhdev, R. R.; Rajamannar, T., WO2004108721 2004), 5-(benzyloxy)-2-methylpyridine (1ah) (Akita, H.; Takano, Y.; Nedu, K.; Kato, K., Tetrahedron-Asymmetry 2006, 17, 1705), 2-phenylpyrimidine (3f) (Bonnet, V.; Mongin, F.; Trecourt, F.; Queguiner, G.; Knochel, P., Tetrahedron 2002, 58, 4429) and 5-(4-hydroxybenzyl)thiazolidine-2,4-dione (5) (Oh, P. J.; Gil, K. Y.; Il, S. H.; Jeong, L. Y.; Mi, K. E., WO2009148195 2009) were prepared according to literature procedures.

NMR chemical shifts are reported in ppm and referenced to residual solvent peaks (CHCl$_3$ in CDCl$_3$: 7.26 ppm for $^1$H and 77.0 ppm for $^{13}$C) or to an external standard (1% CFCl$_3$ in CDCl$_3$: 0 ppm for $^{19}$F). Coupling constants are reported in hertz.

General Procedure for the Fluorination of Pyridines

To an oven-dried vial was added the pyridine substrate (0.50 mmol, 1.0 equiv) and MeCN (5.0-20.0 mL). While the solution was stirring rapidly, AgF$_2$ (219 mg, 1.50 mmol, 3.00 equiv) was added at once. The vial was sealed with a Teflon-lined cap and stirred at room temperature for 1 hour. The reaction was poured into a seperatory funnel containing 20 mL of saturated aqueous NaHCO$_3$ and extracted with 30 mL of Et$_2$O. The organic layer was washed once with 20 mL of brine, dried over MgSO$_4$, and concentrated. The fluoropyridine product was purified by silica gel chromatography.

Synthesis of 2-fluoro-6-phenylpyridine (2a)

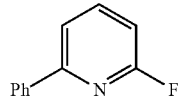

The general procedure for the fluorination of pyridines was performed with 2-phenylpyridine (78 mg, 0.50 mmol, 1.0 equiv), AgF$_2$ (219 mg, 1.50 mmol, 3.00 equiv) and 10 mL of MeCN. The product was purified by silica gel chromatography eluting with 9:1 hexanes:ethyl acetate (R$_f$=0.54) to afford 2a as a clear oil (71 mg, 0.41 mmol, 82% yield).

$^1$H NMR (600 MHz, CDCl$_3$) δ 8.01 (m, 2H), 7.84 (q, J=8.0 Hz, 1H), 7.63 (dd, J=7.5, 2.5 Hz, 1H), 7.50-7.42 (m, 3H), 6.87 (dd, J=8.1, 3.0 Hz, 1H). $^{13}$C NMR (151 MHz, CDCl$_3$) δ 163.3 (d, J=238.1 Hz), 156.1 (d, J=13.4 Hz), 141.6 (d, J=7.7 Hz), 137.4 (s), 129.5 (s), 128.7 (s), 126.8 (s), 117.2 (d, J=3.8 Hz), 107.5 (d, J=37.7 Hz). $^{19}$F NMR (376 MHz, CDCl$_3$) δ -69.6 (s).

Synthesis of 6-fluoro-2-benzoylpyridine (2g)

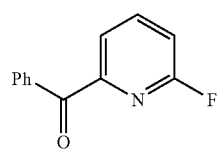 [SMILES: O=C(c1ccccc1)c1cccc(F)n1]

The general procedure for the fluorination of pyridines was performed with 2-benzoylpyridine (92 mg, 0.50 mmol, 1.0 equiv), AgF$_2$ (219 mg, 1.50 mmol, 3.00 equiv) and 10 mL of MeCN. The product was purified by silica gel chromatography eluting with 9:1 hexanes:ethyl acetate (R$_f$=0.48) to afford 2g as a white solid (54 mg, 0.27 mmol, 54% yield).

$^1$H NMR (500 MHz, CDCl$_3$) δ 8.09 (dd, J=8.3, 1.3 Hz, 2H), 8.02 (dd, J=15.5, 7.7 Hz, 1H), 7.95 (ddd, J=7.4, 2.2, 0.7 Hz, 1H), 7.64-7.59 (m, 1H), 7.53-7.47 (m, 2H), 7.17 (ddd, J=8.1, 2.9, 0.7 Hz, 1H). $^{13}$C NMR (151 MHz, CDCl$_3$) δ 191.8 (s), 161.9 (d, J=242.2 Hz), 153.1 (d, J=12.3 Hz), 142.0 (d, J=7.5 Hz), 135.6 (s), 133.1 (s), 130.8 (s), 128.2 (s), 122.1 (d, J=3.9 Hz), 112.8 (d, J=36.9 Hz). $^{19}$F NMR (376 MHz, CDCl$_3$) δ -69.3 (s).

Synthesis of ethyl 6-fluoropicolinate (2h)

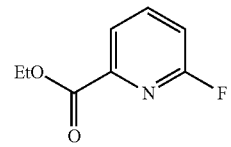

The general procedure for the fluorination of pyridines was performed with ethyl picolinate (76 mg, 0.50 mmol, 1.0 equiv), AgF$_2$ (219 mg, 1.50 mmol, 3.00 equiv) and 10 mL of MeCN. The product was purified by silica gel chromatography eluting with 3:1 hexanes:ethyl acetate (R$_f$=0.56) to afford 2h as a clear oil (57 mg, 0.34 mmol, 67% yield).

$^1$H NMR (500 MHz, CDCl$_3$) δ 8.03 (dd, J=7.6, 1.8 Hz, 1H), 7.95 (dd, J=15.5, 7.7 Hz, 1H), 7.15 (dd, J=8.1, 2.8 Hz, 1H), 4.46 (q, J=7.1 Hz, 2H), 1.43 (t, J=7.1 Hz, 3H). $^{13}$C NMR (151 MHz, CDCl$_3$) δ 163.8 (s), 162.8 (d, J=242.8 Hz), 146.5 (d, J=12.6 Hz), 142.0 (d, J=7.5 Hz), 122.5 (d, J=3.8 Hz), 113.6 (d, J=36.9 Hz), 62.1 (s), 14.1 (s). $^{19}$F NMR (376 MHz, CDCl$_3$) δ -68.7 (s).

Synthesis of N,N-diethyl 6-fluoropicolinamide (2i)

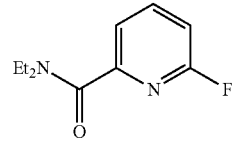

The general procedure for the fluorination of pyridines was performed with N,N-diethyl picolinamide (89 mg, 0.50 mmol, 1.0 equiv), AgF$_2$ (219 mg, 1.50 mmol, 3.00 equiv) and 10 mL of MeCN. The product was purified by silica gel chromatography eluting with 3:1 hexanes:ethyl acetate (R$_f$=0.25) to afford 2i as a clear oil (74 mg, 0.38 mmol, 75% yield).

$^1$H NMR (500 MHz, CDCl$_3$) δ 7.88 (dd, J=15.6, 8.0 Hz, 1H), 7.50 (ddd, J=7.4, 2.1, 0.5 Hz, 1H), 6.97 (ddd, J=8.3, 2.7, 0.4 Hz, 1H), 3.54 (q, J=7.1 Hz, 2H), 3.37 (q, J=7.1 Hz, 2H), 1.25 (t, J=7.1 Hz, 3H), 1.20 (t, J=7.1 Hz, 3H). $^{13}$C NMR (151 MHz, CDCl$_3$) δ 166.6 (s), 162.6 (s), 161.0 (s), 153.1 (d, J=12.9 Hz), 141.8 (d, J=7.6 Hz), 120.5 (d, J=4.1 Hz), 110.1 (d, J=36.5 Hz), 43.1 (s), 40.2 (s), 14.0 (s), 12.6 (s). $^{19}$F NMR (376 MHz, CDCl$_3$) δ -69.9 (s).

Synthesis of ethyl (6-fluoropyridin-2-yl)(methyl)carbamate (2j)

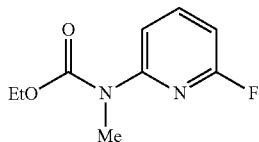 [SMILES: CCOC(=O)N(C)c1cccc(F)n1]

The general procedure for the fluorination of pyridines was performed with ethyl methyl(pyridin-2-yl)carbamate (90 mg, 0.50 mmol, 1.0 equiv), AgF$_2$ (219 mg, 1.50 mmol, 3.00 equiv) and 20 mL of MeCN. The product was purified by silica gel chromatography eluting with 10:1 hexanes:ethyl acetate (R$_f$=0.45) to afford 2j as a clear oil (49 mg, 0.25 mmol, 49% yield).

$^1$H NMR (500 MHz, CDCl$_3$) δ 7.76-7.66 (m, 1H), 6.65-6.57 (m, 1H), 4.26 (q, J=7.1 Hz, 2H), 3.42 (s, 3H), 1.33 (t, J=7.1 Hz, 3H). $^{13}$C NMR (151 MHz, CDCl$_3$) δ 161.5 (d, J=238.4 Hz), 155.0 (s), 153.0 (d, J=13.6 Hz), 141.7 (d, J=7.4 Hz), 114.5 (d, J=4.5 Hz), 103.2 (d, J=36.1 Hz), 62.2 (s), 33.6 (s), 14.4 (s). $^{19}$F NMR (376 MHz, CDCl$_3$) δ −71.3 (s).

Synthesis of 2-fluoro-6-(2-methyl-1,3-dioxolan-2-yl)pyridine (2k)

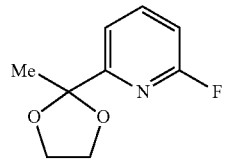

The general procedure for the fluorination of pyridines was performed with 2-(2-methyl-1,3-dioxolan-2-yl)pyridine (83 mg, 0.50 mmol, 1.0 equiv), AgF$_2$ (219 mg, 1.50 mmol, 3.00 equiv) and 10 mL of MeCN. The product was purified by silica gel chromatography eluting with 3:1 hexanes:ethyl acetate with 2% Et$_3$N(R$_f$=0.51) to afford 2k as a clear oil (83 mg, 0.45 mmol, 91% yield).

$^1$H NMR (500 MHz, CDCl$_3$) δ 7.78 (dd, J=15.6, 8.0 Hz, 1H), 7.43 (ddd, J=7.4, 2.3, 0.5 Hz, 1H), 6.86 (ddd, J=8.1, 2.9, 0.4 Hz, 1H), 4.09 (m, 2H), 3.92-3.84 (m, 2H), 1.70 (s, 3H). $^{13}$C NMR (151 MHz, CDCl$_3$) δ 163.1 (d, J=240.4 Hz), 159.9 (d, J=12.0 Hz), 141.4 (d, J=7.4 Hz), 116.5 (d, J=4.0 Hz), 108.7 (d, J=37.1 Hz), 107.7 (s), 64.9 (s), 24.8 (s). $^{19}$F NMR (376 MHz, CDCl$_3$) δ −70.1 (s).

Synthesis of (6-fluoro-2-pyridinyl)methyl acetate (2l)

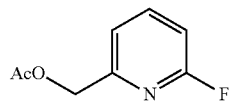 [SMILES: CC(=O)OCc1cccc(F)n1]

The general procedure for the fluorination of pyridines was performed with 2-pyridinylmethyl acetate (76 mg, 0.50 mmol, 1.0 equiv), AgF$_2$ (219 mg, 1.50 mmol, 3.00 equiv) and 10 mL of MeCN. The product was purified by silica gel chromatography eluting with 3:1 hexanes:ethyl acetate (R$_f$=0.52) to afford 2l as a clear oil (60 mg, 0.35 mmol, 71% yield).

$^1$H NMR (600 MHz, CDCl$_3$) δ 7.80 (dd, J=15.7, 8.0 Hz, 1H), 7.23 (dd, J=7.4, 2.1 Hz, 1H), 6.87 (dd, J=8.2, 2.7 Hz, 1H), 5.15 (s, 2H), 2.17 (s, 3H). $^{13}$C NMR (151 MHz, CDCl$_3$) δ 170.3 (s), 163.0 (d, J=240.5 Hz), 154.8 (d, J=10.5 Hz), 141.7 (d, J=7.5 Hz), 118.7 (d, J=3.4 Hz), 108.6 (d, J=36.6 Hz), 65.6 (s), 20.7 (s). $^{19}$F NMR (376 MHz, CDCl$_3$) δ −70.3 (s).

Synthesis of 2-fluorocotinine (2s)

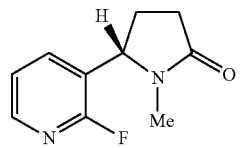 [SMILES: CN1C(=O)CC[C@H]1c1cccnc1F]

The general procedure for the fluorination of pyridines was performed with (−)-cotinine (88 mg, 0.50 mmol, 1.0 equiv), AgF$_2$ (219 mg, 1.50 mmol, 3.00 equiv) and 10 mL of MeCN at 50° C. The major isomer was purified by silica gel chromatography eluting with 99:1 ethyl acetate:triethylamine (R$_f$=0.26) to afford 2s as a clear oil (58 mg, 0.30 mmol, 60% yield).

$^1$H NMR (600 MHz, CDCl$_3$) δ 8.16 (d, J=4.1 Hz, 1H), 7.54 (t, J=8.5 Hz, 1H), 7.24-7.20 (m, 1H), 4.80 (dd, J=8.0, 4.6 Hz, 1H), 2.71 (s, 3H), 2.57-2.38 (m, 4H), 1.87 (m, 1H). $^{13}$C NMR (151 MHz, CDCl$_3$) δ 175.4 (s), 161.1 (d, J=239.1 Hz), 147.0 (d, J=15.0 Hz), 137.7 (d, J=4.6 Hz), 122.9 (d, J=27.4 Hz), 121.9 (d, J=3.7 Hz), 57.7 (s), 29.4 (s), 28.3 (s), 26.5 (s). $^{19}$F NMR (376 MHz, CDCl$_3$) δ −75.6 (s).

Synthesis of N,N-diethyl-2-fluoronicotinamide (2t)

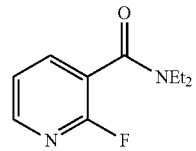

The general procedure for the fluorination of pyridines was performed with N,N-diethylnicotinamide (89 mg, 0.50 mmol, 1.0 equiv), AgF$_2$ (219 mg, 1.50 mmol, 3.00 equiv) and 20 mL of MeCN. Both isomers of the product were purified by silica gel chromatography eluting with 1:1 hexanes:ethyl acetate to afford 2t as a clear oil (63 mg, 0.32 mmol, 64% yield) and iso-2t as a clear oil (6 mg, 0.03 mmol, 6%).

Spectral Data for 2t $^1$H NMR (500 MHz, CDCl$_3$) δ 8.26 (d, J=4.2 Hz, 1H), 7.83-7.77 (m, 1H), 7.26 (dd, J=9.1, 3.0 Hz, 1H), 3.57 (dd, J=14.1, 7.0 Hz, 2H), 3.21 (q, J=7.1 Hz, 2H), 1.26 (t, J=7.1 Hz, 3H), 1.10 (t, J=7.1 Hz, 3H). $^{13}$C NMR (151 MHz, CDCl$_3$) δ 164.2 (d, J=3.9 Hz), 158.4 (d, J=238.0 Hz), 148.2 (d, J=14.3 Hz), 139.4 (d, J=4.5 Hz), 121.5 (d, J=4.1 Hz), 119.9 (d, J=34.4 Hz), 43.0 (s), 39.3 (s), 13.8 (s), 12.6 (s). $^{19}$F NMR (376 MHz, CDCl$_3$) δ −73.0 (s).

Spectral Data for iso-2t

$^1$H NMR (500 MHz, CDCl$_3$) δ 8.28 (d, J=2.4 Hz, 1H), 7.85 (ddd, J=8.3, 7.7, 2.4 Hz, 1H), 7.00-6.97 (m, 1H), 3.55 (br, 2H), 3.28 (br, 2H), 1.20 (br, 6H). $^{19}$F NMR (376 MHz, CDCl$_3$) δ −69.2 (s).

Synthesis of 2-fluoro-3-(2-methyl-1,3-dioxolan-2-yl)pyridine (2u)

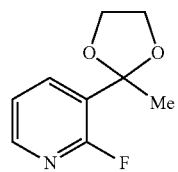

The general procedure for the fluorination of pyridines was performed with 3-(2-methyl-1,3-dioxolan-2-yl)pyridine (83 mg, 0.50 mmol, 1.0 equiv), AgF$_2$ (219 mg, 1.50 mmol, 3.00 equiv) and 20 mL of MeCN. Both isomers of the product were purified by silica gel chromatography eluting with 9:1 hexanes:ethyl acetate to afford 2u as a clear oil (43 mg, 0.23 mmol, 47% yield) and iso-2u as a clear oil (23 mg, 0.13 mmol, 25%).

Spectral Data for 2u

$^1$H NMR (500 MHz, CDCl$_3$) δ 8.15-8.11 (m, 1H), 7.90 (ddd, J=9.6, 7.4, 2.0 Hz, 1H), 7.14 (ddd, J=7.1, 4.9, 1.9 Hz, 1H), 4.10-4.01 (m, 2H), 3.85-3.77 (m, 2H), 1.72 (s, 3H). $^{13}$C NMR (151 MHz, CDCl$_3$) δ 160.6 (d, J=241.6 Hz), 147.1 (d, J=14.9 Hz), 137.9 (d, J=4.5 Hz), 124.9 (d, J=27.9 Hz), 121.0 (d, J=4.4 Hz), 106.4 (d, J=6.6 Hz), 64.8 (s), 25.6 (d, J=3.0 Hz). $^{19}$F NMR (376 MHz, CDCl$_3$) δ −69.2 (s).

Spectral Data for iso-2u

$^1$H NMR (500 MHz, CDCl$_3$) δ 8.31 (s, 1H), 7.85 (td, J=8.1, 2.4 Hz, 1H), 6.88 (dd, J=8.5, 2.8 Hz, 1H), 4.08-4.01 (m, 2H), 3.80-3.73 (m, 2H), 1.63 (s, 3H). $^{13}$C NMR (151 MHz, CDCl$_3$) δ 163.3 (d, J=238.8 Hz), 145.1 (d, J=15.1 Hz), 138.7 (d, J=8.0 Hz), 136.7 (d, J=4.4 Hz), 108.9 (d, J=37.4 Hz), 107.4 (s), 64.6 (s), 27.6 (s). $^{19}$F NMR (376 MHz, CDCl$_3$) δ −72.6 (s).

Synthesis of tert-butyl 2-fluoronicotinate (2v)

The general procedure for the fluorination of pyridines was performed with tert-butyl nicotinate (90 mg, 0.50 mmol, 1.0 equiv), AgF$_2$ (219 mg, 1.50 mmol, 3.00 equiv) and 5 mL of MeCN. Both isomers of the product were purified by silica gel chromatography eluting with 9:1 hexanes:ethyl acetate to afford 2v as a clear oil (41 mg, 0.21 mmol, 42% yield) and iso-2v as a clear oil (21 mg, 0.11 mmol, 21%).

Spectral Data for 2v

$^1$H NMR (600 MHz, CDCl$_3$) δ 8.32 (d, J=4.1 Hz, 1H), 8.28 (t, J=8.4 Hz, 1H), 7.26-7.23 (m, 1H), 1.57 (s, 9H). $^{13}$C NMR (151 MHz, CDCl$_3$) δ 162.2 (d, J=7.9 Hz), 161.5 (d, J=249.2 Hz), 150.9 (d, J=15.3 Hz), 142.9 (s), 121.2 (d, J=4.7 Hz), 115.6 (d, J=24.8 Hz), 82.8 (s), 28.1 (s). $^{19}$F NMR (376 MHz, CDCl$_3$) δ −65.9 (s).

Spectral Data for iso-2v

$^1$H NMR (600 MHz, CDCl$_3$) δ 8.80 (d, J=2.2 Hz, 1H), 8.33 (td, J=8.1, 2.4 Hz, 1H), 6.96 (dd, J=8.5, 2.8 Hz, 1H), 1.59 (s, 9H). $^{13}$C NMR (151 MHz, CDCl$_3$) δ 165.6 (d, J=244.7 Hz), 163.3 (s), 150.1 (d, J=16.4 Hz), 142.4 (d, J=9.2 Hz), 126.1 (d, J=4.5 Hz), 109.2 (d, J=37.5 Hz), 82.3 (s), 28.1 (s). $^{19}$F NMR (376 MHz, CDCl$_3$) δ −65.2 (s).

Synthesis of N,N-diethyl-2-fluoroisonicotinamide (2z)

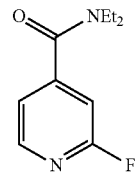

The general procedure for the fluorination of pyridines was performed with N,N-diethyl isonicotinamide (89 mg, 0.50 mmol, 1.0 equiv), AgF$_2$ (219 mg, 1.50 mmol, 3.00 equiv) and 10 mL of MeCN. The product was purified by silica gel chromatography eluting with 3:1 hexanes:ethyl acetate to afford 2z as a clear oil (65 mg, 0.33 mmol, 66% yield).

$^1$H NMR (500 MHz, CDCl$_3$) δ 8.28 (d, J=5.0 Hz, 1H), 7.16-7.14 (m, 1H), 6.91 (d, J=2.3 Hz, 1H), 3.54 (q, J=7.1 Hz, 2H), 3.20 (q, J=7.1 Hz, 2H), 1.25 (t, J=7.1 Hz, 3H), 1.12 (t, J=7.1 Hz, 3H). $^{13}$C NMR (151 MHz, CDCl$_3$) δ 167.2 (d, J=3.4 Hz), 163.6 (d, J=240.7 Hz), 150.1 (d, J=7.1 Hz), 148.3 (d, J=14.8 Hz), 118.6 (d, J=4.3 Hz), 107.0 (d, J=38.8 Hz), 43.1 (s), 39.4 (s), 14.2 (s), 12.7 (s). $^{19}$F NMR (376 MHz, CDCl$_3$) δ −69.0 (s).

Synthesis of ethyl 2-fluoroisonicotinate (2aa)

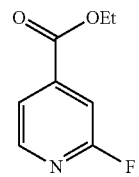 [SMILES: CCOC(=O)c1ccnc(F)c1]

The general procedure for the fluorination of pyridines was performed with ethyl isonicotinate (76 mg, 0.50 mmol, 1.0 equiv), AgF$_2$ (219 mg, 1.50 mmol, 3.00 equiv) and 20 mL of MeCN at 50° C. The product was purified by silica gel chromatography eluting with 3:1 hexanes:ethyl acetate to afford 2aa as a clear oil (37 mg, 0.22 mmol, 44% yield).

$^1$H NMR (500 MHz, CDCl$_3$) δ 8.36 (d, J=5.0 Hz, 1H), 7.74 (d, J=4.9 Hz, 1H), 7.49 (s, 1H), 4.42 (q, J=7.1 Hz, 2H), 1.41 (t, J=7.1 Hz, 3H). $^{13}$C NMR (151 MHz, CDCl$_3$) δ 164.2 (d, J=240.0 Hz), 163.8 (d, J=3.9 Hz), 148.5 (d, J=14.5 Hz), 143.2 (d, J=7.9 Hz), 120.7 (d, J=4.5 Hz), 109.7 (d, J=39.1 Hz), 62.2 (s), 14.1 (s). $^{19}$F NMR (376 MHz, CDCl$_3$) δ −69.5 (s).

Synthesis of methyl 4-chloro-6-fluoropicolinate (2ab)

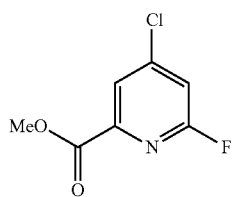 [SMILES: COC(=O)c1cc(Cl)cc(F)n1]

The general procedure for the fluorination of pyridines was performed with methyl 4-chloropicolinate (86 mg, 0.50 mmol, 1.0 equiv), AgF$_2$ (219 mg, 1.50 mmol, 3.00 equiv) and 5 mL of MeCN. The product was purified by silica gel chromatography eluting with 6:1 hexanes:ethyl acetate (R$_f$=0.45) to afford 2ab as a white solid (68 mg, 0.36 mmol, 72% yield).

$^1$H NMR (600 MHz, CDCl$_3$) δ 8.03 (s, 1H), 7.18 (dd, J=2.3, 1.7 Hz, 1H), 4.01 (s, 3H). $^{13}$C NMR (151 MHz, CDCl$_3$) δ 163.3 (s), 163.1 (d, J=244.7 Hz), 148.7 (d, J=9.9 Hz), 146.8 (d, J=14.5 Hz), 123.5 (d, J=4.3 Hz), 113.9 (d, J=40.5 Hz), 53.2 (s). $^{19}$F NMR (376 MHz, CDCl$_3$) δ −67.2 (s).

Synthesis of dimethyl 6-fluoropyridine-2,5-dicarboxylate (2af)

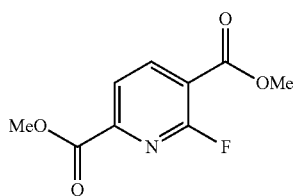 [SMILES: COC(=O)c1ccc(C(=O)OC)c(F)n1]

The general procedure for the fluorination of pyridines was performed with dimethyl pyridine-2,5-dicarboxylate (98 mg, 0.50 mmol, 1.0 equiv), AgF$_2$ (219 mg, 1.50 mmol, 3.00 equiv) and 10 mL of MeCN. The product was purified by silica gel chromatography eluting with 5:1 hexanes:ethyl acetate (R$_f$=0.25) to afford 2af as a white solid (63 mg, 0.30 mmol, 59% yield).

$^1$H NMR (400 MHz, CDCl$_3$) δ 8.54 (dd, J=8.7, 7.8 Hz, 1H), 8.11 (dd, J=7.7, 1.4 Hz, 1H), 4.03 (s, 3H), 3.99 (s, 3H). $^{13}$C NMR (151 MHz, CDCl$_3$) δ 163.5 (s), 162.7 (d, J=7.9 Hz), 160.6 (d, J=253.4 Hz), 148.9 (d, J=13.2 Hz), 144.4 (s), 122.4 (d, J=4.5 Hz), 117.0 (d, J=25.2 Hz), 53.2 (s), 53.0 (s). $^{19}$F NMR (376 MHz, CDCl$_3$) δ −65.1 (s).

Synthesis of 3-(benzyloxy)-2-fluoro-6-methylpyridine (2ah)

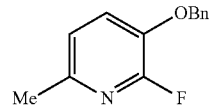

The general procedure for the fluorination of pyridines was performed with 5-benzyloxy-2-methylpyridine (100 mg, 0.50 mmol, 1.0 equiv), AgF$_2$ (219 mg, 1.50 mmol, 3.00 equiv) and 5 mL of MeCN. The product was purified by silica gel chromatography eluting with 6:1 hexanes:ethyl acetate (R$_f$=0.50) to afford 2ah as a clear oil (82 mg, 0.38 mmol, 75% yield).

$^1$H NMR (500 MHz, CDCl3) δ 7.44-7.29 (m, 5H), 7.20 (dd, J=10.2, 8.0 Hz, 1H), 6.89 (d, J=7.9 Hz, 1H), 5.12 (s, 2H), 2.41 (s, 3H). $^{13}$C NMR (151 MHz, CDCl$_3$) δ 153.0 (d, J=237.7 Hz), 147.2 (d, J=12.3 Hz), 139.1 (d, J=25.7 Hz), 135.8 (s), 128.5 (s), 128.2 (s), 127.3 (s), 124.9 (d, J=3.7 Hz), 120.5 (d, J=4.3 Hz), 71.4 (s), 22.6 (s). $^{19}$F NMR (376 MHz, CDCl$_3$) δ −87.4 (s).

Synthesis of 2-(5-ethyl-6-fluoro-2-pyridinyl)ethyl 4-methylbenzenesulfonate (2ai)

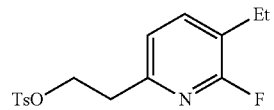 [SMILES: CCc1ccc(CCOS(=O)(=O)c2ccc(C)cc2)nc1F]

The general procedure for the fluorination of pyridines was performed with 2-(5-ethyl-2-pyridinyl)ethyl 4-methylbenzenesulfonate (153 mg, 0.50 mmol, 1.0 equiv), AgF$_2$ (219 mg, 1.50 mmol, 3.00 equiv) and 5 mL of MeCN. The product was purified by silica gel chromatography eluting with 3:1 hexanes:ethyl acetate (R$_f$=0.55) to afford 2ai as a white solid (133 mg, 0.41 mmol, 82% yield).

$^1$H NMR (500 MHz, CDCl$_3$) δ 7.67 (d, J=8.3 Hz, 2H), 7.50 (dd, J=9.9, 7.5 Hz, 1H), 7.28 (d, J=8.1 Hz, 2H), 6.97 (dd, J=7.4, 1.4 Hz, 1H), 4.37 (t, J=6.4 Hz, 2H), 3.01 (t, J=6.4 Hz, 2H), 2.61 (q, J=7.6 Hz, 2H), 2.44 (s, 3H), 1.22 (t, J=7.6 Hz, 3H). $^{13}$C NMR (151 MHz, CDCl$_3$) δ 161.1 (d, J=238.9 Hz), 152.1 (d, J=13.4 Hz), 144.6 (s), 140.2 (d, J=6.2 Hz), 132.5 (s), 129.6 (s), 127.6 (s), 123.3 (d, J=30.9 Hz), 121.1 (d, J=4.0 Hz), 68.8 (s), 36.1 (s), 21.5 (s), 21.4 (s), 13.5 (s). $^{19}$F NMR (376 MHz, CDCl$_3$) δ −75.6 (s).

Synthesis of acyl 2-fluorotropicamide (2aj)

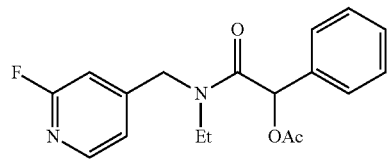 [SMILES: CCN(Cc1ccnc(F)c1)C(=O)C(OC(C)=O)c1ccccc1]

The general procedure for the fluorination of pyridines was performed with acyl tropicamide (163 mg, 0.50 mmol, 1.0 equiv), AgF$_2$ (219 mg, 1.50 mmol, 3.00 equiv) and 20 mL of MeCN at 50° C. The product was purified by silica gel chromatography eluting with ethyl acetate ($R_f$=0.75) to afford 2aj as a clear oil (127 mg, 0.37 mmol, 74% yield).

The compound exists as a 2.5:1 ratio of amide diastereomers on the NMR time scale.

$^1$H NMR (600 MHz, CDCl$_3$) δ 8.15 (d, J=5.1 Hz), 8.09 (d, J=5.1 Hz), 7.43-7.27 (m), 7.24 (d, J=6.7 Hz), 6.93 (d, J=5.0 Hz), 6.89 (d, J=5.0 Hz), 6.64 (s), 4.73-4.50 (m), 4.38-4.17 (m), 4.14-4.09 (m), 3.86 (dd, J=9.2, 5.1 Hz), 3.70 (dq, J=14.0, 7.1 Hz), 3.51-3.38 (m), 3.23-3.13 (m), 2.06 (s), 2.03 (s), 1.23 (dt, J=33.9, 7.1 Hz), 1.10 (t, J=7.1 Hz), 1.05 (t, J=7.1 Hz). $^{13}$C NMR (151 MHz, CDCl$_3$) δ 170.81 (s), 170.51-170.30 (m), 164.04 (d, J=239.0 Hz), 163.90 (d, J=238.3 Hz), 153.02 (d, J=7.6 Hz), 152.40 (d, J=7.4 Hz), 147.79 (d, J=15.2 Hz), 147.37 (d, J=15.3 Hz), 135.00 (s), 134.65 (s), 128.99 (s), 128.93 (s), 127.93 (s), 127.75 (s), 119.70 (d, J=3.9 Hz), 118.88 (d, J=3.9 Hz), 107.33 (d, J=38.1 Hz), 106.69 (d, J=38.5 Hz), 66.30 (s), 66.17 (s), 48.88 (d, J=2.8 Hz), 48.04 (s), 47.50 (s), 42.54 (s), 41.50 (s), 20.57 (s), 20.51 (s), 13.80 (s), 12.19 (s). $^{19}$F NMR (376 MHz, CDCl$_3$) δ −70.9 (s), −71.9 (s).

Synthesis of 8-bromo-2-fluoroquinoline (4b)

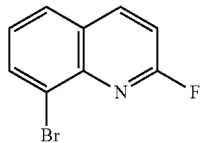 [SMILES: Fc1ccc2cccc(Br)c2n1]

The general procedure for the fluorination of pyridines was performed with 8-bromoquinoline (104 mg, 0.50 mmol, 1.0 equiv), AgF$_2$ (219 mg, 1.50 mmol, 3.00 equiv) and 20 mL of MeCN. The product was purified by silica gel chromatography eluting with 6:1 hexanes:ethyl acetate ($R_f$=0.43) to afford 4b as a white solid (69 mg, 0.31 mmol, 61% yield).

$^1$H NMR (600 MHz, CDCl$_3$) δ 8.28 (t, J=8.3 Hz, 1H), 8.07 (d, J=7.5 Hz, 1H), 7.83 (d, J=8.1 Hz, 1H), 7.41 (t, J=7.8 Hz, 1H), 7.15 (dd, J=8.7, 2.9 Hz, 1H). $^{13}$C NMR (151 MHz, CDCl$_3$) δ 161.4 (d, J=244.2 Hz), 143.1 (d, J=16.3 Hz), 142.7 (d, J=9.9 Hz), 134.1 (s), 127.9 (d, J=1.6 Hz), 127.2 (s), 126.5 (d, J=2.1 Hz), 122.6 (s), 110.9 (d, J=42.4 Hz). $^{19}$F NMR (376 MHz, CDCl$_3$) δ −62.2 (s).

Synthesis of tert-butyl (4-fluoropyrimidin-2-yl)(propyl)carbamate (4i)

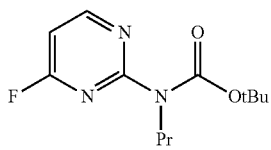

The general procedure for the fluorination of pyridines was performed with tert-butyl (pyrimidin-2-yl)(propyl)carbamate (119 mg, 0.50 mmol, 1.0 equiv), AgF$_2$ (219 mg, 1.50 mmol, 3.00 equiv) and 10 mL of MeCN. The product was purified by silica gel chromatography eluting with 6:1 hexanes:ethyl acetate ($R_f$=0.50) to afford 4i as a clear oil (99 mg, 0.39 mmol, 77% yield).

$^1$H NMR (600 MHz, CDCl$_3$) δ 8.65-8.58 (m, 1H), 6.60 (m, 1H), 3.88 (m, 2H), 1.73-1.63 (m, 2H), 1.53 (s, 9H), 0.91 (m, 3H). $^{13}$C NMR (151 MHz, CDCl$_3$) δ 169.29 (d, J=252.5 Hz), 161.06 (d, J=6.5 Hz), 160.87 (d, J=15.5 Hz), 152.90 (s), 100.89 (d, J=29.6 Hz), 81.63 (s), 49.01 (s), 27.83 (s), 21.73 (s), 10.93 (s). $^{19}$F NMR (376 MHz, CDCl$_3$) δ −61.25 (s).

Synthesis of fluoro-pioglitazone

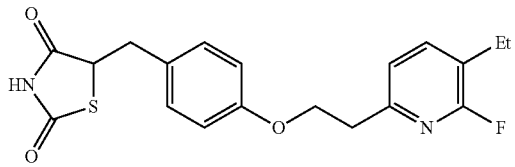 [SMILES: CCc1ccc(CCOc2ccc(CC3SC(=O)NC3=O)cc2)nc1F]

To a vial was added 2ai (323 mg, 1.00 mmol, 1.00 equiv), 5-(4-hydroxybenzyl)thiazolidine-2,4-dione (223 mg, 1.00 mmol, 1.00 equiv), K$_2$CO$_3$ (415 mg, 3.00 mmol, 3.00 equiv) and DMF (5 mL). The resulting reaction mixture was heated at 80° C. for 90 minutes. The reaction mixture was diluted with EtOAc (40 mL) and washed with H$_2$O (3×20 mL) and brine (1×20 mL). The EtOAc layer was dried over MgSO$_4$, and concentrated to an oil. The product was purified by silica gel chromatography eluting with 1:1 hexanes:ethyl acetate ($R_f$=0.64) to afford fluoro-pioglitazone as a light yellow oil (251 mg, 0.670 mmol, 67% yield).

$^1$H NMR (500 MHz, CDCl$_3$) δ 7.51 (dd, J=9.9, 7.5 Hz, 1H), 7.08 (d, J=8.5 Hz, 2H), 6.90 (dd, J=7.4, 1.4 Hz, 1H), 6.79 (d, J=8.5 Hz, 2H), 5.81 (br, 1H), 4.37 (dd, J=9.5, 3.8 Hz, 1H), 3.91 (td, J=7.0, 1.9 Hz, 2H), 3.40 (dd, J=14.1, 3.8 Hz, 1H), 3.04 (dd, J=14.1, 9.5 Hz, 1H), 2.89 (t, J=7.1 Hz, 2H), 2.62 (q, J=7.6 Hz, 2H), 1.21 (t, J=7.6 Hz, 3H). $^{13}$C NMR (151 MHz, CDCl$_3$) δ 173.89 (s), 171.28 (s), 161.29 (d, J=239.9 Hz), 155.56 (s), 153.45 (d, J=12.9 Hz), 140.61 (d, J=6.2 Hz), 130.41 (s), 127.25 (s), 123.44 (d, J=30.4 Hz), 120.73 (d, J=4.0 Hz), 115.62 (s), 51.69 (s), 41.06 (s), 37.67 (s), 33.99 (s), 21.52 (s), 13.51 (s). $^{19}$F NMR (376 MHz, CDCl$_3$) δ −74.91 (d, J=9.8 Hz).

II. Discussion

Novel reactions between AgF$_2$ and a substituted heteroarene (e.g., pyridine) were investigated. Though AgF$_2$ has been demonstrated to react with an excess of benzene in refluxing hexane to form a mixture of fluorinated products (Zweig, A.; Fischer, R. G.; Lancaster, J. E. *J. Org. Chem.* 1980, 45, 3597), a similar reaction with a nitrogen-containing heterocycle has not been disclosed in the art.

Initial studies were performed with 2-phenylpyridine to identify reaction conditions selective for fluorination of the heteroarene over fluorination of the arene. The reaction between 2-phenylpyridine and 3 equivalents of AgF$_2$ in MeCN at room temperature formed 2-fluoro-6-phenylpyridine as the only fluorinated product ($^{19}$F NMR spectroscopy). The only organic material detected by GC was the starting 2-phenylpyridine and the 2-fluoro-6-phenylpyridine product. Reactions performed in solvents other than MeCN did not afford the fluorinated product in appreciable amounts. During the course of the reaction, AgF$_2$ is reduced to AgF, as signified by the formation of a yellow solid (Commercial AgF2 is a black crystalline solid). Although HF is formally generated as a stoichiometric byproduct in the reaction, the yield was not affected by added base. This result is surprising because 2-fluoropyridines are only weakly basic (the pka of the 2-fluoropyridinium ion is –0.44, the pka of the pyridinium ion is 5.17) and 2-phenylpyridinium tetrafluoroborate was unreactive towards AgF$_2$ (Table 1, entry 15).

TABLE 1

Fluorination of 2-phenylpyridine with AgF$_2$[a]

| Entry | Solvent | Additive | Temp (° C.) | 2a (%) |
|---|---|---|---|---|
| 1 | THF | — | rt | 0 |
| 2 | DMF | — | rt | 0 |
| 3 | Toluene | — | rt | 0 |
| 4 | Pentane | — | rt | 0 |
| 5 | MeCN | — | rt | 88 |
| 6 | EtCN | — | rt | 2 |
| 7 | $^i$PrCN | — | rt | 0 |
| 8 | $^t$BuCN | — | rt | 0 |

TABLE 1-continued

Fluorination of 2-phenylpyridine with AgF$_2$[a]

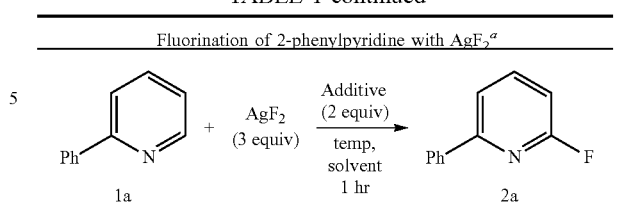

| Entry | Solvent | Additive | Temp (° C.) | 2a (%) |
|---|---|---|---|---|
| 9 | MeCN | — | 50 | 57 |
| 10 | MeCN | — | 80 | 27 |
| 11 | MeCN | KF | rt | 78 |
| 12 | MeCN | CsF | rt | 0 |
| 13 | MeCN | Na$_3$PO$_4$ | rt | 71 |
| 14 | MeCN | Me$_3$py | rt | 45 |
| 15[b] | MeCN | HBF$_4$ | rt | 0 |

[a]Reactions were performed with 0.1 mmol of 2-phenylpyridine and the yields were determined by $^{19}$F NMR spectroscopy with PhCF$_3$ as an internal standard added after the reaction.
[b]Isolated 2-phenylpyridinium tetrafluoroborate was used as the substrate.

The mild reaction conditions identified for the fluorination of 2-phenylpyridine were examined for the fluorination of a broad range of substituted pyridines. The products of these exemmplary reactions are shown in Table 2.

TABLE 2

Fluorination of pyridines with AgF$_2$[a]

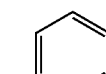

2a, R = Ph, 88% (82%)
2b, R = Et, 94%[b]
2c, R = $^t$Bu, 50%

2d, X = OMe, 57%[b]
2e, X = Cl, 41%[c]
2f, X = Br, 43%[c]

2g, R = Ph, 59% (54%)
2g, R = OEt, 73% (67%)
2l, R = NEt$_2$, 63% (75%)

2j, 62%[d] (49%)

2k, 96% (91%)

2l, 81% (71%)

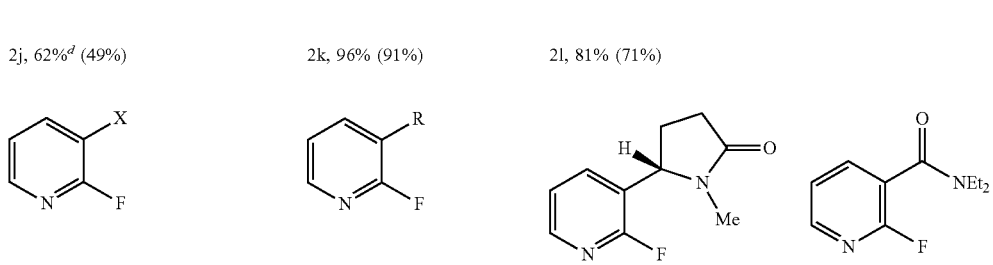

TABLE 2-continued

Fluorination of pyridines with AgF$_2$[a]

$$R\text{-pyridine (1)} + AgF_2 \text{ (3 equiv)} \xrightarrow{\text{MeCN (0.05M), rt, 1 hr}} R\text{-2-fluoropyridine (2)}$$

2m, X = F, 55%[b]
2n, X = Cl, 64%[c]
2o, X = Br, 72%

2p, R = CF$_3$, 97%
2q, R = CN, 53%
2r, R = OMe, 70%

2s, 75%
(60%), 5.3:1

2t, 77%[c] (70%)
4.5:1

2u, 79%[c]
(72%), 2.3:1

2v, 86%[b]
(63%), 2.0:1

2w, R = $^t$Bu, 80%[c]
2x, R = OMe, 75%[b]
2y, R = Cl, 62%[b]

2z, R = NEt$_2$, 76% (66%)
2aa, R = OEt, 51%[da] (44%)

2ab, 74%[b] (72%)

2ac, 57%[c]

2ad, 75%[b]

2ae, 44%[c]

2af, 63% (59%)

2ag, R = Me, 74[b]
2ah, R = OBn, 99%[b] (75%)

2ai, 93%[b] (82%)

2aj, 70%[be] (74%)

[a]Reactions were performed with 0.1 mmol of pyridine to determine yields by $^{19}$F NMR spectroscopy with PhCF$_3$ as an internal standard. Isolated yields for reactions performed on a 0.5 mmol scale are shown in parenthesis.
[b]Reactions performed at 0.1M.
[c]Reactions performed at 0.025M.
[d]Reactions performed for 2 hrs.
[e]Reactions performed at 50° C.

The fluorination occurred with pyridines containing both electron-donating and electron-withdrawing groups at each position of the ring. Substrates containing ketones, esters, amides, acetals, protected alcohols and amines, nitriles, alkyl tosylates, and enolizable carbonyls underwent the fluorination in good yield (the direct fluorination of pyridines with F$_2$ gas has been demonstrated for alkyl, chloro, and ester substituted pyridines in 31-70% yields. The direct fluorination with F$_2$ gas of pyridines containing benzy, acyl, or bromo substituents resulted in less than 30% yield. See, a. Simons, J. H. U.S. Pat. No. 2,447,717 1948; b. Vanderpuy, M. *Tetrahedron Lett* 1987, 28, 255; and c. Chambers, R. D.; Parsons, M.; Sandford, G.; Skinner, C. J.; Atherton, M. J.; Moilliet, J. S. *J Chem Soc Perk T*1 1999, 803). Notably, bromide and chloride substituents in the 2-position of the pyridine, which are susceptible to nucleophilic displacement, remained intact during the reaction. Carboxylic acids and aldehydes were transformed to the corresponding acyl fluorides. The reactions with pyridines containing functional groups in the 3 positions formed the 2-fluoro-3-functionalized pyridine products preferentially. In some cases, a mixture of 2,3 and 2,5 functionalized products were formed, and these products were separable by silica gel chromatography. The C—H fluorination reaction also proceeded with several disubstituted pyridines.

To demonstrate the utility of these reactions directly on medicinally important compounds, we performed the fluorination of acetyl-Mydriacil (tropicamide), an anticholinergic drug. This compound (1aj), containing a base-sensitive acetate and an acidic α-phenyl amide, reacted with $AgF_2$ to form 2aj in 74% isolated yield.

The reaction conditions developed for the fluorination of pyridines led to the fluorination of a range of other 6-membered nitrogen heterocycles. Quinolines, pyrazines, pyrimidines, and pyridazines reacted to afford mono-fluorinated products in modest to good yields. Pyrimidines containing an alkyl, aryl, oxygen, or nitrogen group in the 2-position reacted to form the corresponding 4-fluoropyrimidines in good yield. However, unsubstituted pyrimidine did not react to form any fluorinated products under the reaction conditions. $AgF_2$ reacted with 5-membered heterocycles to form complex mixtures of products (5-membered heterocycles are not tolerated in the fluorination of pyridines).

isolation in high yield; in these cases the yields determined by $^{19}F$ NMR spectroscopy are reported. In each reaction, only the mono-fluorination product is observed. Furthermore, the organic material in these reactions consists solely of the mono-fluorinated product and unreacted starting material (GC/MS). The presence of fluorine adjacent to nitrogen decreases the basicity and polarity of the products, relative to the starting material, allowing for easy purification by silica gel chromatography or acid/base extractions. For example, the Rf value of 2-fluoro-6-phenylpyridine on silica is 0.54, while that of 2-phenylpyridine is 0.08 (9:1 hexanes:ethyl acetate).

$AgF_2$ is an attractive fluorine source because it is commercially available in multi-gram quantities and is cheaper than many common fluorinating reagents. The cost of $AgF_2$ is $1.83/mmol compared to $2.41/mmol for Selectfluor, the cheapest and most common electrophilic fluorinating reagent. Prices are based on the 2013 Sigma-Aldrich catalog prices for 10 grams of reagent. Although stoichiometric amounts of silver are used in these reactions, the silver byproducts can be readily recovered by filtration and recycled to $AgF_2$ or other silver salts. The reactions with $AgF_2$ are insensitive to light and were performed in clear glass vessels.

The ability to conduct the fluorination reaction on multi-gram scale was assessed by conducting the reaction of 2,5-substituted pyridine 1ai on a 5 mmol scale. This reaction

TABLE 3

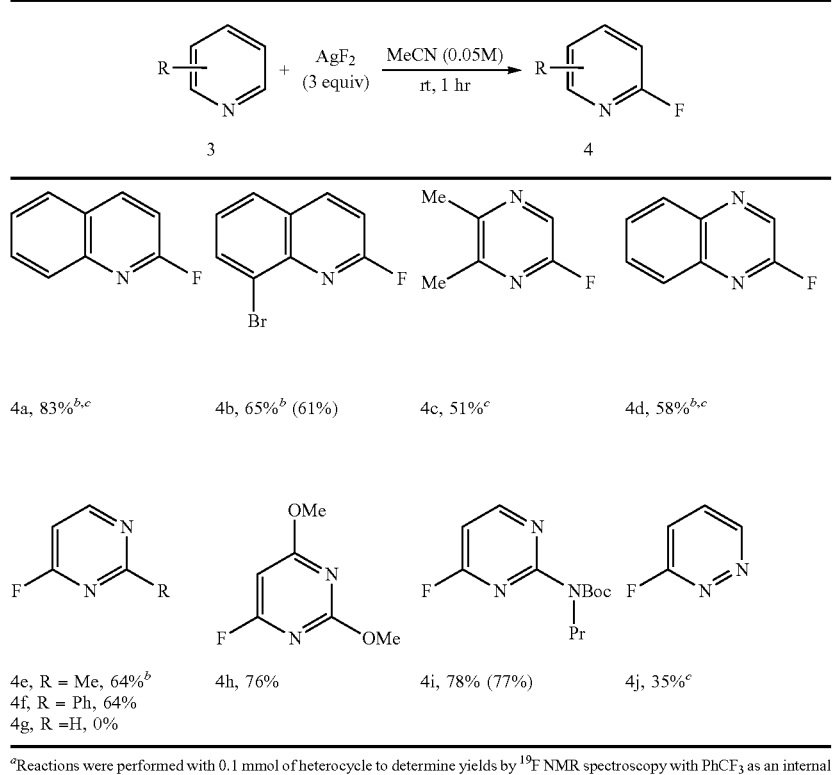

[a]Reactions were performed with 0.1 mmol of heterocycle to determine yields by $^{19}F$ NMR spectroscopy with PhCF$_3$ as an internal standard. Isolated yields for reactions performed on a 0.5 mmol scale are shown in parenthesis.
[b]Reactions performed at 0.025M.
[c]Reactions performed at 50° C.

Isolated yields of the reactions performed with 0.5 mmol of substrate were comparable to the yields determined by $^{19}F$ NMR spectroscopy for reactions performed on a 0.1 mmol scale. The volatility of some products prevented their led to 1.34 grams of pure, isolated 2ai (83% yield). The product of this reaction was then converted in one step to a fluorinated analogue of the anti-diabetic drug pioglitazone (Actos).

Scheme 3. Gram scale fluorination with AgF$_2$ and the synthesis of fluoro-pioglitazone

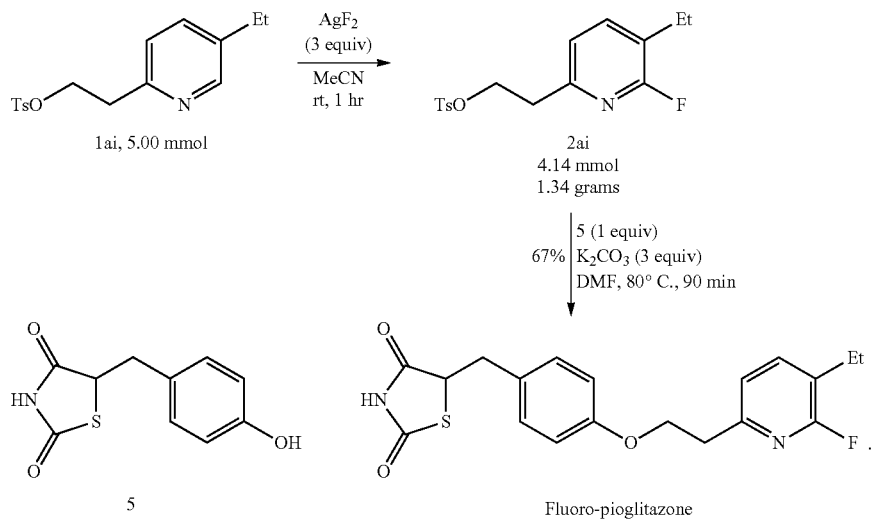

Further exemplary synthetic applications for 2-fluoropyridines are shown in Scheme 4.

Scheme 4. Exemplary synthetic applications of 2-fluoropyridines.

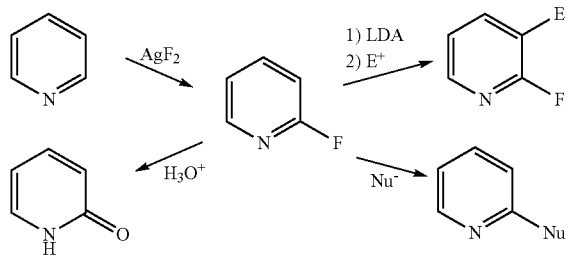

Example 2

The present invention also provides methods for the late-stage functionalization of pyridines and diazines that would address the limitations of the regioselectivity and scope of C—H functionalizations of heteroarenes. The approach was inspired by the value of borylation reactions developed in the authors' laboratory to create synthetic intermediates that can be converted to a variety of functionalized products (Hartwig, J. F. Acc. Chem. Res. 2012, 45, 864.). The present example demonstrates that the C—H fluorination of pyridines and diazines at the position α to nitrogen with AgF$_2$ according to the present invention could be used for the late-stage functionalization of medicinally relevant compounds because pyridines and diazines are contained in many such compounds and the 2-fluoro group could be replaced with a wide range of nucleophiles.

The present example sets forth exemplary mild conditions for the S$_N$Ar reaction of fluoroheteroarenes, an assessment of the potential of the fluorination and S$_N$Ar reactions to be conducted with complex structures, and the application of these findings to the development of late-stage functionalizations of complex heterocyclic compounds by the combination of C—H fluorination and S$_N$Ar reactions (CHF—S$_N$Ar, Scheme 1C). In addition to revealing the potential of this reaction for the functionalization of complex heteroarenes, we demonstrate how the combination of CHF and S$_N$Ar creates routes to several active pharmaceutical ingredients that occur in higher yields and fewer steps than previously reported syntheses of these molecules.

Results and Discussion

1. Conditions for the Nucleophilic Aromatic Substitution of 2-Fluoropyridines

S$_N$Ar reactions of 2- or 4-halopyridines comprise a site-specific method to synthesize substituted pyridines (Terrier, F. Modern Nucleophilic Aromatic Substitution; Wiley-VCH: Weinheim; Hoboken, 2013.). However, this approach requires initial synthesis and isolation of halogenated pyridines that are typically prepared from pyridine-N-oxides or hydroxypyridines with neat POX$_3$ (X=Br, Cl) at high temperatures.

TABLE 1

Reaction Conditions for the S$_N$Ar of 2-fluoropyridines.

R = 6-Ph or 5-Me

| NuH | Base | Solvent | Temp | Time (h) | Conv. |
|---|---|---|---|---|---|
| 1°, 2°, or 3° alcohol | KO$^t$Bu | THF | 50 °C | 3 | 100% |
| ArOH | KO$^t$Bu | DMF | 80° C. | 6 | 100% |
| 1° or 2° amine | $^i$Pr$_2$NEt | DMSO | 120° C. | 18 | 100% |
| Amide (N—H) | NaH | DMF | 100° C. | 3 | 100% |
| N-heterocycle | NaH | DMF | 100° C. | 1-3 | 100% |
| KCN (3 equiv) | — | DMSO | 120° C. | 18 | ~80% |
| NaSR | — | THF | 50° C. | 3 | 100% |

The majority of S$_N$Ar reactions with halopyridines have been performed with chloropyridines. Chloropyridines are more available commercially than other halopyridines, but the reactions of fluoropyridines are likely to be faster than those of chloropyridines. As for $S_NAr$ reactions of arenes, the $S_NAr$ reactions of pyridines and diazines are likely to be accelerated by the high electronegativity of fluorine. Indeed, the reaction of 2-fluoropyridine with NaOEt in EtOH is 320 times faster than the reaction of 2-chloropyridine (Schlosser, M.; Rausis, T. *Helvetica Chimica Acta* 2005, 88, 1240.). This higher reactivity of fluoropyridines could allow $S_NAr$ reactions to occur under conditions that are mild enough to allow this class of reaction to occur on complex molecules; however, a more detailed assessment of the rates and yields for the $S_NAr$ reactions of fluoropyridines and diazines would be needed to predict the scope of the $S_NAr$ process and a method to create the 2-fluoropyridines and diazines that could be conducted in a typical laboratory on complex pyridines and diazines would be required.

Thus, to develop a sequence of C—H bond fluorination and $S_NAr$, we first evaluated conditions to conduct $S_NAr$ reactions of 2-fluoropyridines. Although $S_NAr$ reactions of electron-deficient fluoroarenes and chloropyridines are commonplace (Terrier, F., supra), few studies have been performed on $S_NAr$ reactions of fluoropyridines ((a) Loupy, A.; Philippon, N.; Pigeon, P.; Galons, H. *Heterocycles* 1991, 32, 1947; (b) Cherng, Y. H. *Tetrahedron* 2002, 58, 4931; (c) Thomas, S.; Roberts, S.; Pasumansky, L.; Gamsey, S.; Singaram, B. *Org. Lett.* 2003, 5, 3867; (d) Klapars, A.; Waldman, J. H.; Campos, K. R.; Jensen, M. S.; McLaughlin, M.; Chung, J. Y. L.; Cvetovich, R. J.; Chen, C. Y. *J. Org. Chem.* 2005, 70, 10186; (e) Seki, K.; Ohkura, K.; Terashima, M.; Kanaoka, Y. *Heterocycles* 1994, 37, 993). The majority of the published reactions of 2-fluoropyridines have been conducted with unsubstituted 2-fluoropyridine; a few examples were conducted with 2-fluoropyridines containing a single bromide substituent. Moreover, these reactions were performed under conditions involving strong nucleophiles and bases at high temperatures (up to 130° C.), neat reagents, microwave heating, strong reducing agents ($LiBH_3NR_2$), or toxic solvents (HMPA), and these conditions are unlikely to tolerate the functional groups found in complex molecules relevant to medicinal chemistry.

To identify conditions for the $S_NAr$ reaction that would tolerate common functionality, we studied reactions of unactivated 2-fluoropyridines with nucleophiles derived from alcohols, phenols, amines, amides, N-heterocycles, cyanide and thiols under relatively mild conditions. The reaction conditions we identified afforded quantitative conversion to the substitution products, as indicated by GC/MS and TLC (Table 1). Reactions with KCN proceeded in approximately 80% yield. Variation of the cyanide source, stoichiometry, temperature and solvent did not increase the yield, but the initial conditions did form the cyanopyridine product in a synthetically useful yield. Having developed a set of $S_NAr$ reactions that occur under mild conditions, we explored the tandem fluorination-substitution process.

For the $S_NAr$ reactions to occur in tandem with C—H fluorination, the MeCN and silver salts from the fluorination reaction needed to be removed. Filtering the fluorination reactions through a short silica-filled pipette and evaporating the solvent was sufficient to perform the subsequent $S_NAr$ reactions. Yields of the $S_NAr$ reactions conducted after filtering the fluorination reaction through Celite were low, due to the presence of soluble Ag salts.

2. Convenient Protocols for Performing the Fluorination of Pyridines and Diazines For the fluorination-$S_NAr$ sequence to be used broadly, procedures for conducting the reaction without specialized equipment for excluding air and moisture are needed. $AgF_2$ is a hygroscopic solid that decomposes in the presence of water. Therefore, during our initial study the fluorination reactions were assembled in a glovebox with rigorously dried MeCN.[10] However, despite the water sensitivity of $AgF_2$, simple procedures can be followed for conducting the reactions without rigorous exclusion of air or moisture.

To assess the impact of water and oxygen on the yield of the fluorination reaction of complex molecules, we performed a series of experiments with ($CO_2Me$)-vismodegib, a drug recently approved for the treatment of basal-cell carcinoma (Table 2). Assembling the fluorination reaction in a glovebox (oxygen and water content <1 ppm), in an oven-dried vial, with MeCN that had been rigorously dried over $CaH_2$, afforded the fluorinated vismodegib derivative in 99% yield by $^{19}F$ NMR spectroscopy.

TABLE 3

Tandem C—H Fluorination and $S_NAr$.

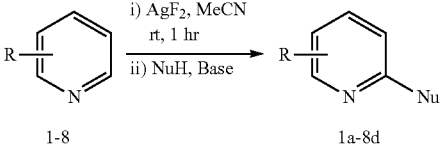

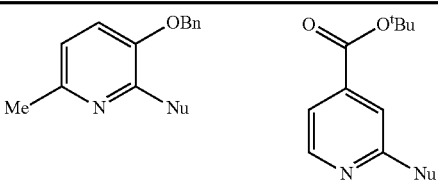

F, (88%)
1a, OBu, 84%
1b, O$^i$Pr, 84%
1c, O$^t$Bu, 81%
1d, O(p-BuC$_6$H$_4$), 73%[b]
1e, NHC$_8$H$_{17}$, 60%

F, (99%)
2a, OBu, 77%
2b, O$^i$Pr, 78%
2c, O$^t$Bu, 77%
2d, pyrrolyl, 59%

F, (64%)
3a, O(m-BrC$_6$H$_4$), 40%
3b, pyrrolidinonyl, 46%
3c, pyrrolyl, 45%

TABLE 3-continued

Tandem C—H Fluorination and S$_N$Ar.

R—[pyridine]  
i) AgF$_2$, MeCN, rt, 1 hr  
ii) NuH, Base  
→ R—[pyridine]-Nu 1-8 → 1a-8d 1f, morpholino, 75%  
1g, CN, 61%

[Structure: THP-OCH$_2$-pyridine with Br and Nu]

F, (87%)  
4a, O$^i$Pr, 74%  
4b, NHC$_8$H$_{17}$, 70%  
4c, S$^t$Bu, 51%

[Structure: pyrimidine with OMe, MeO, and Nu]

F, (76%)  
5a, O$^t$Bu, 71%  
5b, NHC$_8$H$_{17}$, 71%  
5c, pyrrolidinonyl, 63%

[Structure: pyrimidine with CF$_3$, $^i$PrO, and Nu]

F, (75%)  
6a, O(m-OMeC$_6$H$_4$), 50%[b]  
6b, morpholino, 50%

[Structure: pyridine with Cl, Et$_2$N-C(O)-, and Nu]

F, (82%)  
7a, O$^t$Bu, 70%  
7b, NBu$_2$, 71%  
7c, indolyl, 61%

[Structure: quinoxaline with Cl, N(Boc)(Bn), and Nu]

F, (99%)  
8a, OBu, 92%  
8b, furfurylamino, 82W%[c]  
8c, imidazolyl, 83%  
8d, 3,5-Me$_2$pyrazolyl, 68%

[a]Isolated yields from the 2-step sequence for reactions performed with 0.2 mmol of heteroarene. Yields in parentheses were determined by $^{19}$F NMR spectroscopy for the independent fluorination reaction.  
[b]The isolated product contained ~5% of an inseparable impurity.  
[c]The Boc-group was cleaved during the S$_N$Ar reaction Since the use of a glovebox is not practical for all chemists, we studied the effects of weighing the solid reagents in air and assembling the reaction using standard air-free techniques. A reaction was assembled by adding the pyridine substrate to a dry vial in air and adding MeCN that had been dried over CaH$_2$. AgF$_2$ was weighed quickly in air, added to the pyridine solution, and the vial was sealed under an atmosphere of N$_2$. The reaction assembled in this manner afforded the 2-fluoropyridine product in 84% yield, only a slight decrease in yield compared to the reaction assembled entirely in the glovebox. Performing the reaction in a similar manner with a non-dried vial, and sealing the reaction under an atmosphere of air (2 mL of MeCN in a 4 mL vial; 2 mL headspace of air) resulted in a similar yield of the fluoropyridine product (79%).

Acetonitrile dried with 5 weight % of 3 Å molecular sieves for 24 h was a suitable solvent; The reaction of (CO$_2$Me)-vismodegib with AgF$_2$ assembled by weighing the solid reagents in air in a non-dried vial sealed under an atmosphere of air, afforded the fluorinated product in 85% yield. The water content in MeCN dried over 5 wt % molecular sieves for 24 hours is near 4 ppm, and the water content further decreases with time. The water content of commercial "anhydrous" MeCN is below 10 ppm water and should be equally suitable for this reaction.

Finally, the same reaction was assembled in air with ACS grade MeCN directly from a commercial bottle that had been opened and used over the course of a year; a noticeable decrease in yield to 65% was observed, but a substantial amount of product was still formed. Together, these results demonstrate that these fluorination reactions can be conveniently assembled completely in air, without the use of a glovebox or air-free techniques, and with MeCN dried over molecular sieves, even though AgF$_2$ is sensitive to water and should be stored under an inert atmosphere. Reactions performed on the bench top occur in yields that are comparable to those performed under rigorously anhydrous reaction conditions.

TABLE 2

Assessing the Impact of Water and Air on the Fluorination Reaction with AgF$_2$.

[Structure: (CO$_2$Me)-Vismodegib] → AgF$_2$ (3 equiv), MeCN, rt, 2 hr

TABLE 2-continued

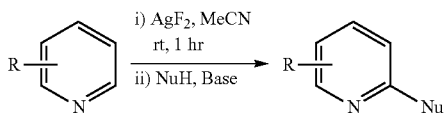

| Method of drying MeCN | Rxn vial dried | Solids weighed | Atmosphere | Yield (NMR) |
|---|---|---|---|---|
| $CaH_2$ | Yes | In glovebox | $N_2$ | 99% |
| $CaH_2$ | Yes | In air | $N_2$ | 84% |
| $CaH_2$ | No | In air | Air | 79% |
| Molecular Sieves | No | In air | Air | 85% |
| None | No | In air | Air | 65% |

[a]Reactions were performed with 0.2 mmol of ($CO_2Me$)-vismodegib with 2 mL of MeCN in 4 mL vials.

$AgF_2$ is supplied as a black, microcrystalline solid, which should be stored under an inert atmosphere. Because $AgF_2$ undergoes decomposition with moisture, a noticeable color change from black to yellow or brown is observed when it is stored in air. For all reactions reported here, $AgF_2$ was used as received from Alfa Aesar and stored under a nitrogen atmosphere in a plastic bottle. In our experience, reactions with $AgF_2$ supplied from Strem occurred in comparable rates and yields to those performed with $AgF_2$ purchased from Alfa Aesar.

3. Scope of the Tandem C—H Fluorination and Nucleophilic Aromatic Substitution of Pyridines Having identified convenient methods for conducting both the fluorination and $S_NAr$ reactions and having developed a protocol to conduct the two reactions in sequence, we investigated the scope of the fluorination-$S_NAr$ process. Representative examples illustrating the scope of the combined reactions are shown in Tables 3 and 4. Yields given are for isolated products starting from the heteroarene. The yields for the fluorination step are also shown to illustrate how the values for the two-step process compare to those of the first step.

TABLE 4

Tandem C—H Fluorination and $S_NAr$ of Medicinally Important Compounds.

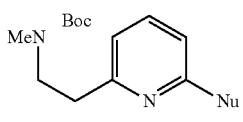
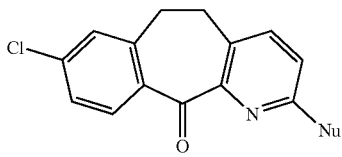

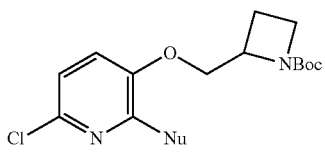

(Boc)-Betahistine
F, (98%)
9a, OBu, 60%
9b, morpholino, 47%
9c, indolyl, 51%

Precursor to Loratadine and Desloratadine
F, (53%)
10a, 1,2-isopropylideneglycerol, 47%[b]
10b, piperidino, 31%[b]
10c, pyrazolyl, 40%[b]

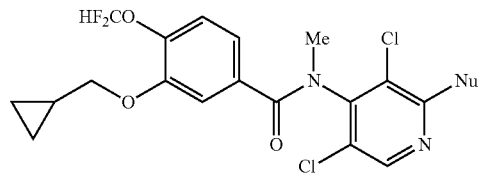

(Boc)-Tebanicline
F, (65%)
11a, OBu, 53%
11b, $NHC_8H_{17}$, 56%
11c, imidazolyl, 38%

(Me)-Roflumilast
F, (69%)
12a, $O^iPr$, 44%
12b, $NHC_8H_{17}$, 47%

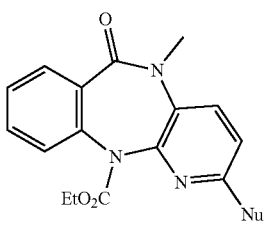
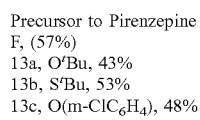

Precursor to Pirenzepine
F, (57%)
13a, $O^tBu$, 43%
13b, $S^tBu$, 53%
13c, O(m-$ClC_6H_4$), 48%

TABLE 4-continued

Tandem C—H Fluorination and S$_N$Ar of Medicinally Important Compounds.

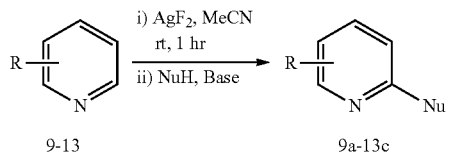

[a] Isolated yields from the 2-step sequence for reactions performed with 0.2 mmol of heteroarene. Yields in parentheses were determined by $^{19}$F NMR spectroscopy for the independent fluorination reaction.
[b] The isolated product contained ~5% of an inseparable impurity.

A variety of pyridines that are sterically (2, 4, 11, 12, 14, 15) and/or electronically deactivated (2, 9, 13, 15) towards S$_N$Ar reactions afforded the substitution products in good yields. Substrates containing alkyl groups in the 2-position reacted uneventfully (2, 4, 9, 14), while analogous reactions with pyridine N-oxides are known to result in substitution of a C—H bond on the alkyl group (Scheme 1B). A wide range of functional groups were tolerated, including ethers, halides, ketones, acetals, esters, amides, ethyl and t-butyl carbamates, nitriles, and sulfones. It is notable that the azetidine in 11 (Table 4) did not undergo ring opening, a competing reaction observed under acidic conditions.

The reactions of chloropyridines 7 and 11 revealed a high selectivity for substitution of a fluoride over a chloride under the S$_N$Ar reaction conditions shown in Table 1. This high selectivity, along with the high functional group compatibility, is attributed to the milder reaction conditions we developed for the S$_N$Ar reaction at the 2-fluoro position, relative to the conditions typically used to conduct substitutions with 2-fluoropyridines. In sum, this work shows that fluoropyridines undergo substitution reactions under conditions much milder than previously reported and can be performed in the presence of a wide range of functional groups, including electrophilic functional groups.

4. Tandem C—H Fluorination and Nucleophilic Aromatic Substitution of Diazines Six-membered heteroarenes containing two nitrogen atoms (diazines) are prevalent subunits in medicinal chemistry. Radical addition reactions to diazines are commonplace (Scheme 1A), but a single example of nucleophilic addition of a heteroatom to a diazine-N-oxide for C—H functionalization (Scheme 1B) has been demonstrated (Keith, J. M. *J. Org. Chem.* 2008, 73, 327). Like pyridines, diazines react with AgF$_2$ with exclusive selectivity for fluorination adjacent to nitrogen (Fier, P. S.; Hartwig, J. F. *Science* 2013, 342, 956). Thus, we considered that the combination of C—H bond fluorination and S$_N$Ar reactions could be conducted with these heterocycles to form functionalized diazine products. Indeed, pyrimidines (5, 6) and pyrazines (8) reacted in the 2-step sequence following the standard conditions we developed for the fluorination and S$_N$Ar reactions reported in Table 1. This sequence allowed several poly-substituted diazines to be prepared through C—H functionalization. Because the conditions for both the fluorination and the S$_N$Ar reactions with diazines are the same as those for pyridines, the tolerance of the reactions toward functional groups on pyridines and diazines should be comparable. This C—H fluorination-S$_N$Ar sequence was also applied to the synthesis of a reverse transcriptase inhibitor containing a tetra-substituted pyrimidine (vide infra).

5. Late-Stage Functionalization of Complex Molecules Via Tandem C—H Fluorination and Nucleophilic Aromatic Substitution With conditions established for the fluorination and S$_N$Ar reactions of pyridines and diazines, we evaluated this sequence for the late-stage functionalization of more complex molecules in medicinal chemistry. First, we used our tandem sequence to prepare several 2-substituted derivatives of (Boc-protected) betahistine (9), a histamine agonist used in the treatment of Meniere's disease. Reaction of 9 with AgF$_2$ formed the corresponding 2-fluoropyridine in nearly quantitative yield (98%). This electronically deactivated fluoropyridine intermediate reacted with nucleophiles derived from butanol, morpholine and indole to provide several 2-substituted analogs of betahistine. Although betahistine is a relatively simple compound that can be prepared in one step form 2-vinylpyridine, the synthesis of derivatives that are similar to those we report here would require 2-substituted-6-vinylpyridines. Few such pyridines are commercially available (2-bromo-6-vinylpyridine is listed at $360 for 250 mg from Matrix Scientific.). Thus, our CHF—S$_N$Ar strategy for late-stage functionalization avoids lengthy synthetic sequences to prepare derivatives of betahistine.

We also conducted the fluorination of compound 10, the direct precursor to loratadine (Claritin) and desloratadine (Clarinex), two common antihistamines. Compound 10 is prepared in 2 steps from 3-methylpicolinic acid under relatively harsh reaction conditions ("BuLi, KO$^t$Bu for the first step; SOCl$_2$, AlCl$_3$ for the second step). Therefore, the synthesis of 2-substituted derivatives of 10 would require access to the appropriately substituted 3-methylpicolinic acid, which could require several steps to prepare, and an additional two-step sequence to construct the tricycle for each derivative. We prepared various analogs of 10 more directly through fluorination and S$_N$Ar reactions to form the corresponding 2-alkoxy, 2-amino, and 2-pyrazolyl substituted derivatives. It is worthy to note that the substituents we installed in 10a-10c would be unlikely to tolerate the conditions of a de-novo synthesis of similar analogs of 10.

Our C—H functionalization method also gave access to a series of (Boc-protected) derivatives of tebanicline (11), a potent non-opiod analgesic that is structurally related to several nicotinic acetylcholine receptor agonists. As mentioned above, no ring-opening of the azetidine or substitution of the chloride was observed. De-novo syntheses of compounds similar to 11a-11c would require access to 2-substituted-3-hydroxy-6-chloropyridine substrates and an additional C—O bond forming reaction to complete the synthesis of each derivative.

The sequence of C—H bond fluorination and S$_N$Ar also led to a convenient synthesis of 2-alkoxy and 2-amino analogs of roflumilast (12). Roflumilast is a recently approved PDE-4 inhibitor used in the treatment of chronic obstructive pulmonary disease. The reported syntheses of this compound involve amide-bond formation with 3,5-dichloro-4-aminopyridine. Thus, the syntheses of the 2-substituted analogs we report would require access to 2-alkoxy or 2-amino-3,5-dichloro-4-aminopyridine, for which none are commercially available. Therefore, preparing derivatives of roflumilast would mandate multi-step syntheses of the appropriate pyridine, in addition to performing the subsequent amide-bond formation for each derivative. In contrast, the CHF—$S_N$Ar strategy we report allows rapid access to analogs that would otherwise require several synthetic steps to prepare.

In a similar manner, analogs of the precursor to pirenzepine (13), a benzodiazepine based M1 selective antagonist used for the treatment of ulcers, were prepared. The sequence was used to install alkoxy, thio, and aryloxy substituents at the 2-position in good overall yields. Competing reactions at the electrophilic ethyl carbamate were not observed. The synthesis of the core of 13 requires 3 steps from 2-chloro-3-aminopyridine.

6. Relative Rates for the Fluorination of Pyridines and Diazines Having Different Electronic Properties Because many medicinally important compounds contain multiple heteroaryl rings it would be valuable if the fluorination were selective for the functionalization of one type of ring system over another. The proposed mechanism for the fluorination of pyridines and diazines with $AgF_2$ (eq 1) is initiated by coordination of the basic nitrogen to silver. This coordination could cause a more basic heterocycle to be more reactive than a less basic heterocycle. However, the second step in the proposed mechanism is addition of fluoride to the π system, which would be favored for a more electron-deficient heteroarene. Finally, the third step, a formal oxidation of the heterocycle through hydrogen-atom abstraction, would likely be favored for a more electron-rich substrate. Our previous studies of the selectivity between pyridine and pyridine-$d_5$ demonstrated that coordination of $AgF_2$ to pyridine is reversible and that cleavage of the C—H bond is irreversible.

TABLE 5

Competition Experiments between Electronically Different Pyridines and Diazines with $AgF_2$.

|  | R = Et | R = OMe | R = Cl |
|---|---|---|---|
| Substrate pKa: | 5.97 | 3.28 | 0.72 |
| Yield of independent fluorination reaction: | 94% | 57% | 41% |
| 2-Fluoropyridine product ratio: | >20 | <1 | — |
|  | >20 | — | <1 |
|  | — | >20 | <1 |

TABLE 5-continued

|  | A | B | C |
|---|---|---|---|
| Substrate pKa: | 5.99 | 2.3 | 2.2 |
| Yield of independent fluorination reaction: | 80% | 64% | 51% |
| Fluoroheteroarene product ratio: | >20 | <1 | — |
|  | >20 | — | <1 |
|  | — | 3.3 | 1 |

[a]Product ratios were determined by $^{19}$F NMR spectroscopy of the crude reaction mixture after quenching with aqueous $NaHCO_3$.

To determine how the electronic properties of the heteroarene influence the relative rates of fluorination, we conducted a series of competition experiments. In these experiments, $AgF_2$ was allowed to react with a 1:1 mixture of two different pyridines and diazines. Because the yield of the fluorination reactions conducted with a large excess of pyridine, relative to $AgF_2$, is low, reactions containing 1 equivalent of each heteroarene (0.1 mmol each) and 2 equivalents of $AgF_2$ (0.2 mmol) were run, and the reactions were quenched after 15 minutes so that the selectivities were being measured at low conversion (25±2%). Competition experiments between 2-ethyl, 2-methoxy, and 2-chloropyridine were conducted; the steric properties of these substrates are similar to each other, but the basicity of the heterocycles differ incrementally from each other by ~2.6 $pK_a$ units. Competition experiments were also conducted between alkyl-substituted pyridines, pyrimidines, and pyrazines containing two available C—H bonds for fluorination. The results of these competition experiments are shown in Table 5. These data show that more Lewis basic pyridines undergo the C—H fluorination reactions in preference to less Lewis basic pyridines. Moreover, exclusive selectivity for fluorination of a 4-alkyl pyridine over two alkyl-substituted diazines was observed; the competition between 2-methylpyridimidine and 2,3-dimethylpyrazine showed that the pyrimidine was the more reactive diazine by a factor of 3.3.

The results of these competition experiments contrast with what would be predicted based only on the relative rates of independent reactions between each substrate and $AgF_2$. 2-Ethylpyridine reacts with 2 equivalents of $AgF_2$ to give 38% yield of the 6-fluoropyridine after 15 minutes. Similarly, 2-methoxypyridine reacts in 36% yield, and 2-chloropyridine reacts in 9% yield after 15 minutes. Because the rates for fluorination of 2-ethylpyridine and 2-methoxypyridine are comparable, and because $AgF_2$ is present in excess, little selectivity for 2-ethylpyridine over 2-methoxypyridine would be expected based on these data alone. However, $AgF_2$ has negligible solubility in MeCN; therefore, competitive binding of the two substrates to the limited amount of available $AgF_2$ likely results in fluorination of the more basic pyridine.

To assess the relative reactivity of multiple pyridines in the context of a medicinally important compound, we conducted the fluorination and $S_NAr$ reaction of etoricoxib (eq 2), a selective COX-2 inhibitor used in the treatment of arthritis. This compound contains two different pyridine rings. The more electron-rich ring contains methyl and 2-pyridyl substituents, and the less electron-rich ring contains chloro, aryl, and 3-pyridyl substituents. This molecule reacted with $AgF_2$ with complete selectivity for fluorination of the more basic pyridine system, as predicted from the results in Table 5. No product resulting from fluorination of the 3-chloropyridine was observed. Following this site-selective fluorination, several derivatives of etoricoxib containing pendant alkoxy, amino, cyano, and pyrazolyl units were prepared.

7. Site-Selectivity for the Fluorination of 3,5-Disubstituted Pyridines

Many medicinally active pyridines contain two inequivalent C—H bonds that could undergo fluorination with $AgF_2$. We previously demonstrated that several 3-substituted pyridines undergo fluorination with exclusive selectivity to form the 2-fluoro-3-substituted pyridine product. The 3-substituted pyridines that react selectively at the 2-position include those containing 3-halo, alkoxy, cyano, or $CF_3$ groups. 3-Substituted pyridines that give a mixture of 2-fluoropyridine isomers include those containing 3-alkyl, 3-$CO_2R$, and 3-$C(O)NR_2$ substituents. It was unclear from these results if 3,5-disubstituted pyridines would undergo the fluorination selectively.

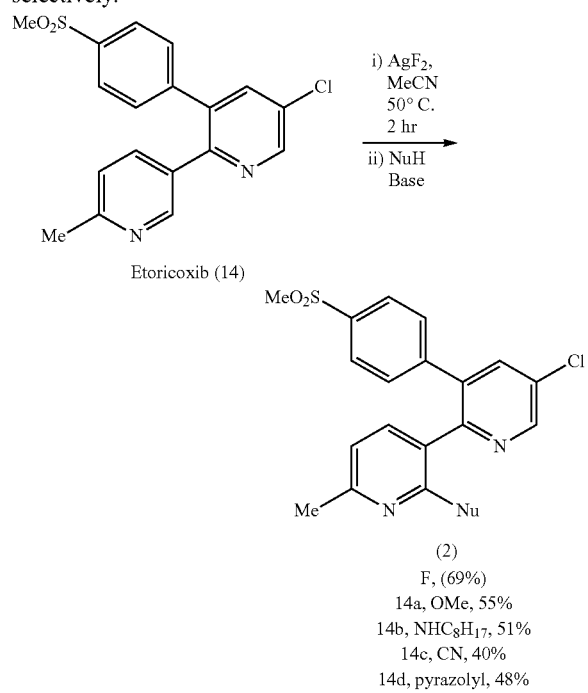

Etoricoxib (14)

(2)
F, (69%)
14a, OMe, 55%
14b, $NHC_8H_{17}$, 51%
14c, CN, 40%
14d, pyrazolyl, 48%

A set of 3,5-disubstituted pyridines containing phenyl, cyano, benzyloxy, bromo, methyl, and $CF_3$ substituents was prepared. The fluorination of the 15 unsymmetrical pyridines containing these substituents occurred with poor site-selectivity (from 1:1 up to 6:1), with the exception of the benzyloxy-substituted pyridines. The 3-benzyloxy substituted pyridines containing various substituents in the 5-position reacted with $AgF_2$ with modest to high selectivity (4.2:1 to 20:1) for fluorination adjacent to the ether substituent (Table 6).

Having shown that an alkoxy group can lead to selective fluorination of a 3,5-disubstituted pyridine, we exploited this selectivity to conduct the late-stage fluorination of a medicinally relevant, 3,5-disubstituted pyridine. The core of crizotinib (eq 3), a drug used for the treatment of metastatic non-small cell lung cancer, contains such a heteroaromatic unit.

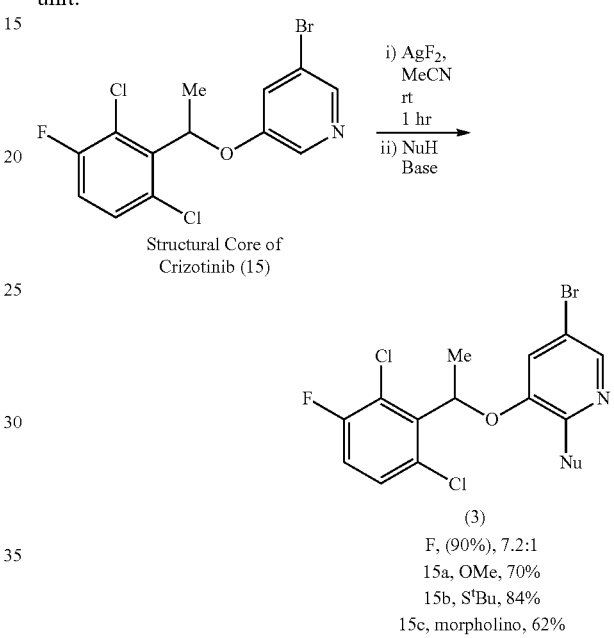

Structural Core of Crizotinib (15)

(3)
F, (90%), 7.2:1
15a, OMe, 70%
15b, $S^tBu$, 84%
15c, morpholino, 62%

Reaction of crizotinib with $AgF_2$ gave products reflecting a 7.2:1 selectivity for fluorination adjacent to oxygen. This selectivity is lower than that observed for the fluorination of 3-bromo-5-benzyloxypyridine (Table 6), likely due to the steric hindrance of the arylethoxy substituent. To determine if the lower selectivity of this substrate is due to the greater steric hindrance of the benzyloxy group of Crizotinib than that of a simple benzyloxy substrate, the fluorination reaction was also performed with a 2,6-dimethylphenyl arylethoxy substrate. This compound reacted in 62% yield with similar 5.9:1 selectivity for fluorination adjacent to the ether substituent. Thus, the selectivity is lower for reactions of pyridines containing more hindered benzyloxy groups, but is still significant. The steric hindrance of the arylethoxy substrates disfavors both the second and third steps in our proposed mechanism (eq 1), leading to an increase in the relative amount of product from fluorination adjacent to the bromide.

Even though the 2-fluoro-3-benzyloxypydridine intermediate is both sterically and electronically deactivated towards $S_NAr$, several 2-substituted derivatives were prepared under the standard conditions for the $S_NAr$ step shown in Table 1. Even a secondary amine reacted with the 2-fluoropyridine to form the sterically congested product 15c. The isomeric products prepared from 15 after C—H bond fluorination-$S_NAr$ reactions were not separable by standard silica gel chromatography, even though the 2-fluoropyridine isomers could be separated by HPLC and GC.

8. Limitations of the C—H Fluorination and S$_N$Ar Reactions

Although we have demonstrated that the C—H fluorination and S$_N$Ar reactions occur with broad scope and can be conducted on complex molecules, there are some limitations. As we reported previously, the fluorination reaction is not compatible with free amines or alcohols, carboxylic acids, aldehydes, or electron-rich 5-membered heterocycles; however, several protected derivatives of these groups are tolerated by AgF$_2$. In addition, we have found that pyridines or diazines containing multiple electron-withdrawing substituents undergo the fluorination reaction in lower yields than those containing electron-neutral or electron-donating groups. Examples of substrates that reacted with AgF$_2$ in low yields (0-30%) are shown in Table 7. Although the Boc-protected derivative of HG-10-102-01 reacted with AgF$_2$ in low yield, a similar tetra-substituted pyrimidine reacted in high yield for the synthesis of etravirine (vide infra).

TABLE 6

Fluorination of 3,5-Disubstituted Pyridines.

| X | Temp (° C.) | concentration (M) | ratio (D:E) | Combined yield (D + E) |
|---|---|---|---|---|
| Br | 50 | .050 | 15:1 | 49% |
| Cl | 50 | .025 | 8.1:1 | 64% |
| Me | 50 | .025 | >20:1 | 62% |
| Ph | 50 | .050 | 4.2:1 | 68% |
| CN | 50 | .025 | 12:1 | 67% |
| CF$_3$ | rt | .050 | 20:1 | 85% |

We have demonstrated that a simple set of S$_N$Ar reaction conditions can be employed for substitution reactions on a variety of 2-fluoroheteroarenes. However, we did find substrates that underwent competing side-reactions faster than they underwent S$_N$Ar (Table 7).

TABLE 7

Substrates that Reacted in Low Yields for the C—H Fluorination or S$_N$Ar Reactions.

(Boc)$_2$-HG-10-102-01
Low yield for fluorination

Quinmerac, $^t$Bu-ester
Low yield for fluorination (Boc)-Fluopicolide
No fluorination Zopiclone Analog
No fluorination R = Me, Ac, Piv
Tropicamide derivatives
>65% yield for fluorination
Retro-Michael addition during S$_N$Ar Bisacodyl
93% yield for fluorination
Acetate cleavage during S$_N$Ar R = Me, Ac, Piv
Precursor to Nexium
>90% yield for fluorination
Low reactivity in S$_N$Ar Fluorinated analogs of tropicamide underwent retro-Michael addition under the basic reaction conditions. Although we demonstrated that tert-butyl esters remain intact during the $S_NAr$ reactions (Table 3, substrate 3), we found that aryl acetates are cleaved faster than substitution of fluoride. This cleavage was observed when attempting $S_NAr$ reactions of bisacodyl. Finally, very electron-rich and sterically hindered pyridines, such as the precursor to Nexium, underwent the $S_NAr$ step in low yields; more forcing conditions resulted in the formation of side-products.

9. Applications of C—H Fluorination and $S_NAr$ for the Synthesis of Medicinal Compounds Having demonstrated the potential of the C—H fluorination-$S_NAr$ sequence for the late-stage derivatization of medicinally important compounds, we sought to evaluate whether the same strategy could create shorter and higher-yielding synthetic routes to the same types of compounds. Although this chemistry requires stoichiometric silver and is not designed for process-scale chemistry, the strategy of C—H fluorination and $S_NAr$ can be useful in discovery chemistry. One example of a synthesis that could be simplified by the fluorination and substitution process is the synthesis of the simple compound 6-(methylamino)-2-pyridineethanol (Scheme 2, 16). Compound 16 is a precursor to several important compounds, including the integrin inhibitor SB-273005 (Scheme 2C). Although 16 is structurally simple, the two reported syntheses of 16 by medicinal chemists were conducted in 5 and 7 steps from 2-amino-6-methylpyridine (Scheme 2A). We considered that the 2-methylamino group could be installed through C—H bond fluorination and $S_NAr$ from a derivative of 2-pyridineethanol.

Scheme 2. Synthesis of 6-(methylamino)-2-pyridineethanol through C—H Fluorination.

A: Medicinal chemistry syntheses of 16

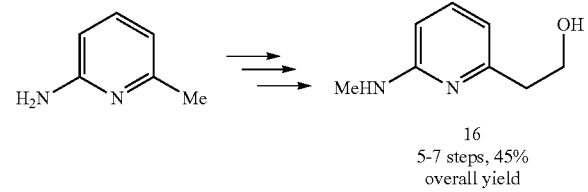

16
5-7 steps, 45% overall yield

B: Synthesis of 16 via C—H Fluorination/$S_NAr$

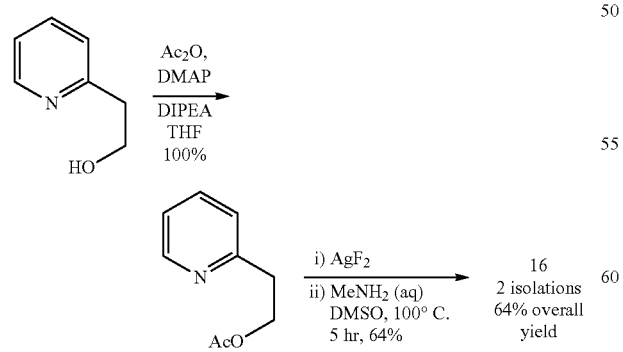

C: 16 as a precursor to medicinal compounds

16 $\xrightarrow{\text{2 steps}}$

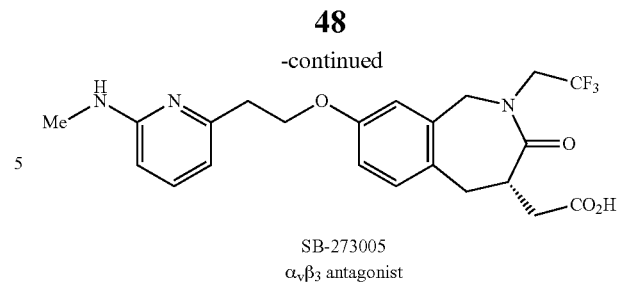

SB-273005
$\alpha_v\beta_3$ antagonist

Fluorination did not occur on the free alcohol, but it did occur after protecting the alcohol as an ester. An acetyl protecting group was chosen because it could be cleaved in concert with the $S_NAr$ reaction. The fluorination of acetylated 2-pyridineethanol occurred in 88% yield (by $^{19}F$ NMR spectroscopy). Treatment of the crude mixture from the fluorination step with aqueous $MeNH_2$ in DMSO led to formation of the methylaminopyridine unit and cleaveage of the acetyl-group to reveal the free alcohol. This route gave 16 with only 2 isolations in 64% overall yield, a significantly shorter and higher-yielding approach than the reported syntheses requiring 5 or 7 steps. Although our route requires stoichiometric silver, it is worthy to note that an improved process used to prepare 30 grams of 16 still required 4 steps and occurred in only 39% overall yield.

The combination of C—H bond fluorination and $S_NAr$ also shortened the synthesis of PF-1247324, a potent and selective $Na_v1.8$ inhibitor (Scheme 3). The medicinal chemistry route to this compound comprised 6 steps and occurred in less than 1% yield; an advanced intermediate was outsourced for the kilogram-scale synthesis of PF-1247324. Our route to this compound began with the fluorination of methyl 5-bromopicolinate. The fluoropyridine intermediate contains two electrophilic sites for nucleophilic substitution: a methyl ester and a 2-fluoropyridine. We demonstrated (Tables 3 and 4) that substitution at the fluorine of a 2-fluoropyridine can occur in the presence of auxiliary electrophilic functional groups, including a tert-butyl ester. However, we considered that conditions could be identified to transform the methyl ester to the N-methyl amide without substitution of the fluoride. The reaction between the fluoropyridine methyl ester with aqueous $MeNH_2$ in THF formed a mixture of products resulting from substitution of both methoxide and fluoride. However, simply changing the reaction solvent from THF to MeOH allowed for the selective transformation of the methyl ester to the N-methyl amide without substitution of the fluoride.

Scheme 3. Synthesis of PF-1247324 through C—H Fluorination

A: Medicinal chemistry synthesis of PF-1247324

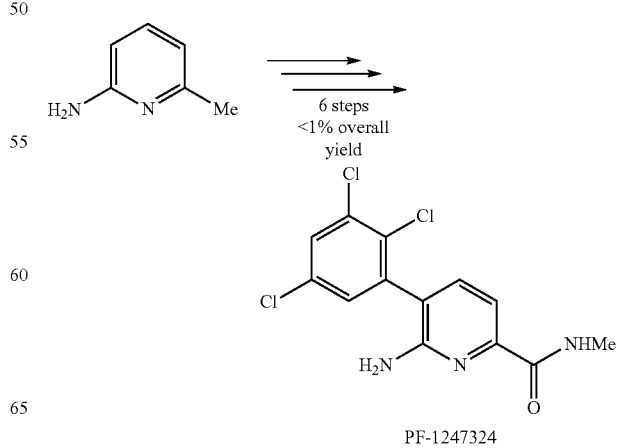

PF-1247324

-continued
B: Synthesis of PF-1247324 via C—H fluorination/S$_N$Ar

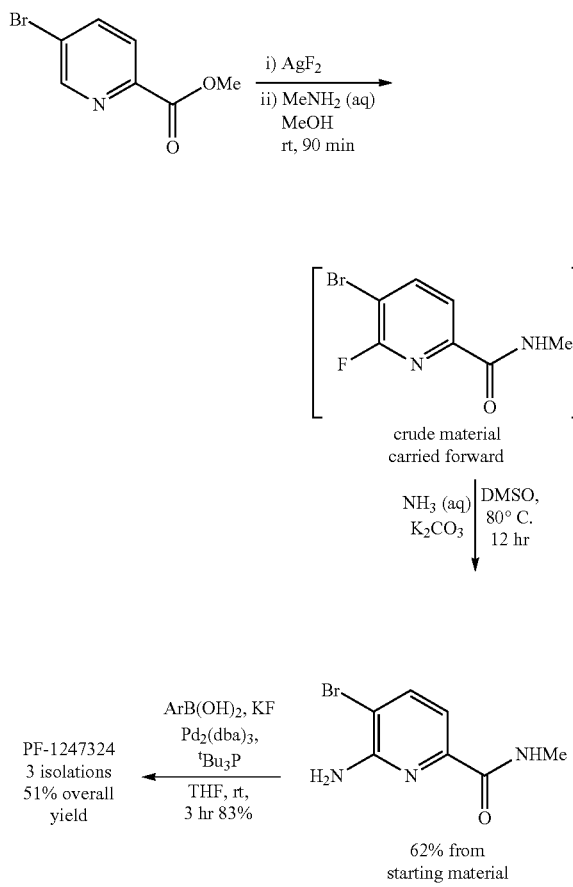

Scheme 4. Synthesis of Intelence (Etravirine) through C—H Fluorination

A: Medicinal chemistry synthesis of etravirine

B: Synthesis of etravirine via C—H fluorination/S$_N$Ar

After aqueous workup, the crude reaction mixture was treated with ammonium hydroxide in DMSO to substitute an NH$_2$ group for the fluoride. Finally, the 3-bromopyridine was subjected to the reported Suzuki cross-coupling reaction conditions to provide the title compound. By our route, the synthesis of PF-1247324 involving C—H fluorination was completed with just three isolated intermediates in 51% overall yield, a major improvement in yield and step count over the published synthesis. Furthermore, the route performed by medicinal chemists required 120 hours of total reaction time, while the route we report here required less than 18 hours.

Finally, we used our chemistry to prepare the non-nucleoside reverse transcriptase inhibitor Intelence (etravirine, Scheme 4), a compound used in the treatment of HIV. The route to this compound developed by medicinal chemists occurred in 5 steps and 9% yield from N-(4-cyanophenyl) guanidine hydrochloride. An alternative route used to prepare etravirine on kilogram scale required 4 steps and occurred in 30% yield.

Our synthesis of etravirine began with substitution of the 4-chloro substituent in 2,4-dichloro-5-bromopyrimidine with 2,6-dimethyl-4-cyanophenol, from which the solid product was isolated after the addition of water. Next, substitution with 4-aminobenzontirile and Boc-protection in-situ was conducted, and the product was isolated in 88% yield. The installation of a protecting group for the N—H bond was necessary for the subsequent fluorination reaction to proceed. The synthesis of etravirine was then completed by C—H fluorination of the pyrimidine (71% yield by $^{19}$F NMR spectroscopy), substitution with aqueous ammonia, and addition of HCl$_{(aq)}$ to cleave the Boc group. Through this route, etravirine was prepared with three isolated intermediates in 45% overall yield in under 6 hours of total reaction time.

CONCLUSION

In summary, in exemplary embodiments, the present invention provides a broadly applicable strategy for the diverse, site selective C—H functionalization of pyridines and diazines. The reaction sequence occurs to provide alkoxy, aryloxy, amino, amido, heteroaryl, thio, and cyano substituted heterocycles that can be difficult to access through traditional methods. This tandem sequence is attractive for the direct diversification of heteroarenes, due to the exquisite site-selectivity for C—H functionalization and the mild reaction conditions. In addition, high site-selectivity for the fluorination of substrates containing more than one heteroarene or more than one reactive C—H bond is possible using this chemistry. Finally, the process of fluorination and $S_NAr$ can allow medicinal compounds containing substituted pyridines and diazines to be prepared by short synthetic routes. We anticipate that these reactions will find immediate use for both late-stage functionalization and efficient syntheses of complex molecules. We aimed to develop a method for the late-stage functionalization of pyridines and diazines that would address the limitations of the regioselectivity and scope of C—H functionalizations of heteroarenes. The present invention provides a general route for the C—H fluorination of pyridines and diazines at the position a to nitrogen with $AgF_2$ and utilizing the fluorinated analogues from this method as precursors for the late-stage functionalization of compounds, e.g., medicinally relevant compounds, because pyridines and diazines are contained in many such compounds and the 2-fluoro group could be replaced with a wide range of nucleophiles.

In various embodiments, the present invention provides mild conditions for the $S_NAr$ reaction of fluoroheteroarenes, an assessment of the potential of the fluorination and $S_NAr$ reactions to be conducted with complex structures, and the application of these findings to the development of late-stage functionalizations of complex heterocyclic compounds by the combination of C—H fluorination and $S_NAr$ reactions (CHF—$S_NAr$, Scheme 1C). In addition to revealing the potential of this reaction for the functionalization of complex heteroarenes, we demonstrate how the combination of CHF and $S_NAr$ creates routes to several active pharmaceutical ingredients that occur in higher yields and fewer steps than previously reported syntheses of these molecules.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reaction mixture for mono-fluorinating a nitrogen atom-containing heteroarene precursor compound at a carbon atom adjacent said nitrogen atom, said reaction mixture comprising:
   (i) said heteroarene precursor compound, said compound optionally substituted at one or more positions of the heteroarene ring;
   (ii) $AgF_2$; and
   (ii) an organic solvent.

2. The reaction mixture according to claim 1, wherein said precursor compound is of the formula:

wherein
A is selected from N and $CR^4$;
D is selected from N and $CR^5$;
E is selected from N and $CR^6$;
G is selected from N and $CR^7$;
J is selected from N and $CR^8$,
wherein
$R^4$, $R^5$, $R^6$, $R^7$ and $R^8$ are independently selected from H, substituted or unsubstituted alkyl, substituted or unsubstituted heteroalkyl, substituted or unsubstituted aryl, substituted or unsubstituted heteroaryl, halogen, CN, $CF_3$, acyl, —$SO_2NR^9R^{10}$, —$NR^9R^{10}$, —$OR^9$, —$S(O)_2R^9$, —$C(O)R^9$, —$COOR^9$, —$CONR^9R^{10}$, —$S(O)_2OR^9$, —$OC(O)R^9$, —$C(O)NR^9R^{10}$, —$NR^9C(O)R^{10}$, $NR^9C(O)NR^{10}R^{11}$, $C(NR^9)R^{10}$, $NR^9SO_2R^{10}$ and —$NO_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl;
wherein
$R^9$, $R^{10}$, and $R^{11}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^9$, $R^{10}$, and $R^{11}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

3. The reaction mixture according to claim 2, wherein said precursor compound is of the formula:

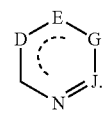

4. The reaction mixture according to claim 2, wherein said precursor compound is of a formula selected from:

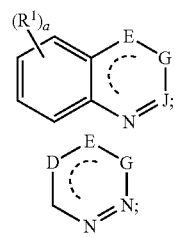

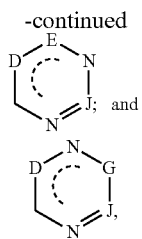

and wherein a is an integer from 0 to 4; and each $R^1$ is independently selected from substituted or unsubstituted alkyl, substituted or unsubstituted heteroalkyl, substituted or unsubstituted aryl, substituted or unsubstituted heteroaryl, halogen, CN, $CF_3$, acyl, $—SO_2NR^2R^3$, $—NR^2R^3$, $—OR^2$, $—S(O)_2R^2$, $—C(O)R^2$, $—COOR^2$, $—CONR^2R^3$, $—S(O)_2OR^2$, $—OC(O)R^2$, $—C(O)NR^2R^3$, $—NR^2C(O)R^3$, $—NR^2SO_2R^3$, $NR^2C(O)NR^3R^{12}$, $C(NR^2)R^3$, and $—NO_2$, wherein two or more $R^1$ moieties together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl, wherein $R^2$, $R^3$, and $R^{12}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^2$, $R^3$, and $R^{12}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

5. The reaction mixture according to claim 1, wherein said solvent is $CH_3CN$.

6. The reaction mixture according to claim 1, wherein said precursor compound is a substituted or unsubstituted diazine or a substituted or unsubstituted triazine.

7. The mixture according to claim 1, wherein said reaction mixture further comprises a fluorinated product derived from said precursor compound, said fluorinated product having the formula:

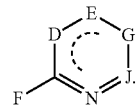

8. The reaction mixture according to claim 1, wherein said reaction mixture is essentially free of difluorinated product.

9. The reaction mixture according to claim 1, wherein said reaction mixture is essentially free of added base.

10. The reaction mixture according to claim 1, said reaction mixture is essentially free of a source of fluoride other than $AgF_2$.

11. The reaction mixture according to claim 1, wherein the ratio of precursor compound to $AgF_2$ is from about 1:1 to about 1:5.

12. The reaction mixture according to claim 1, wherein the ratio of precursor compound to $AgF_2$ is about 1:3.

13. The reaction mixture according to claim 1, wherein said precursor compound is further substituted with a member selected from amine, ether, caroxylic acid, amide, ester, halide, protected alcohol and a combination thereof.

14. The reaction mixture according to claim 1, wherein said precursor compound is a member selected from a substituted or unsubstituted quinoline, pyrazine, pyrimidine, and pyridazine.

15. The reaction mixture according to claim 1, wherein said precursor is other than an unsubstituted pyrimidine.

16. The reaction mixture according to claim 1, wherein said precursor is other than a five-membered nitrogen-containing heteroarene.

17. A method for mono-fluorinating a nitrogen atom-containing heteroarene compound at a carbon α to said nitrogen atom, said method comprising:
(a) forming a reaction mixture according to claim 1; and
(b) incubating said reaction mixture under conditions appropriate to mono-fluorinate said nitrogen-containing heteroarene compound at said carbon atom α to said nitrogen atom.

18. The method according to claim 17, wherein said reaction mixture is incubated at about 25° C.

19. The method according to claim 17, wherein said reaction mixture is incubated for about one hour.

* * * * *

UNITED STATES PATENT AND TRADEMARK OFFICE
CERTIFICATE OF CORRECTION

PATENT NO. : 9,701,635 B2
APPLICATION NO. : 14/907694
DATED : July 11, 2017
INVENTOR(S) : John Hartwig et al.

Page 1 of 1

It is certified that error appears in the above-identified patent and that said Letters Patent is hereby corrected as shown below:

In the Specification

In Column 1, please amend the paragraph below the STATEMENT AS TO RIGHTS TO INVENTIONS MADE UNDER FEDERALLY SPONSORED RESEARCH AND DEVELOPMENT as follows:

This invention was made with Government support under Grant No. GM 055382 awarded by the National Institutes of Health. The Government has certain rights in the invention.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*